(12) United States Patent
Carroll et al.

(10) Patent No.: US 12,039,417 B2
(45) Date of Patent: Jul. 16, 2024

(54) APPARATUS AND METHOD FOR ASSESSING A CHARACTERISTIC OF A PLANT

(71) Applicant: Vivent sárl, Crans-près-Céligny (CH)

(72) Inventors: Caleb Carroll, Alberta (CA); Nigel Christopher Wallbridge, Vaud (CH); Nicholas Barker, Durham (GB); Laura Raileanu, Neuchatel (CH); Fabien Dutoit, Orbe (CH); Marco Mazza, Fribourg (CH); Cedric Camps, Valais (CH); Daniel Tran, Valais (CH); Carrol Annette Plummer, Vaud (CH)

(73) Assignee: VIVENT SA, Crans-Près-Céligny (CH)

( * ) Notice: Subject to any disclaimer, the term of this patent is extended or adjusted under 35 U.S.C. 154(b) by 585 days.

(21) Appl. No.: 16/821,213

(22) Filed: Mar. 17, 2020

(65) Prior Publication Data
US 2020/0302338 A1 Sep. 24, 2020

(30) Foreign Application Priority Data
Mar. 18, 2019 (GB) .................................. 1903652

(51) Int. Cl.
*G06N 20/00* (2019.01)
*G01N 33/00* (2006.01)

(52) U.S. Cl.
CPC ......... *G06N 20/00* (2019.01); *G01N 33/0098* (2013.01)

(58) Field of Classification Search
CPC ...... A01G 27/00; A01G 7/00; G01N 33/0098; G06N 20/00; G06N 20/10
See application file for complete search history.

(56) References Cited

U.S. PATENT DOCUMENTS 3,967,198 A * 6/1976 Gensler ................. A61B 5/24
324/692
6,870,376 B1 3/2005 Gensler
(Continued)

FOREIGN PATENT DOCUMENTS

EP 3693735 8/2020
WO WO 2007/128122 A1 11/2007
(Continued)

OTHER PUBLICATIONS

United Kingdom Search Report for corresponding Application No. GB1903652.4, dated Aug. 21, 2019—3 pages.
(Continued)

*Primary Examiner* — Yoshihisa Ishizuka
(74) *Attorney, Agent, or Firm* — Dority & Manning, P.A.

(57) ABSTRACT

There is provided a method of assessing a characteristic of a plant (2), comprising: obtaining a training dataset, wherein the training dataset comprises first data characterising a first electrical signal obtained from a first plant during a first time period when a stressor is present in the first plant or a growth environment of the first plant, second data characterising a second electrical signal obtained from the first plant during a second time period when a stressor is not present in the first plant or the growth environment of the first plant, and third data indicative of a characteristic of the first plant during the first time period and a characteristic of the first plant during the second time period; training a machine learning model based upon the training dataset; obtaining a third electrical signal from a second plant; and assessing, using the trained machine learning model, a characteristic of the second plant based upon the third electrical signal.

17 Claims, 8 Drawing Sheets

(56) References Cited

U.S. PATENT DOCUMENTS

| | | | |
|---|---|---|---|
| 2015/0015697 A1* | 1/2015 | Redden | A01C 21/007 |
| | | | 382/110 |
| 2017/0032258 A1* | 2/2017 | Miresmailli | G06N 20/00 |
| 2017/0042098 A1* | 2/2017 | Moshelion | A01G 7/00 |
| 2019/0028492 A1* | 1/2019 | Coleman | G08B 21/182 |
| 2019/0050948 A1 | 2/2019 | Perry et al. | |
| 2019/0059202 A1 | 2/2019 | Lorek | |
| 2022/0075344 A1* | 3/2022 | Gillberg | A01G 22/20 |

FOREIGN PATENT DOCUMENTS

| | | |
|---|---|---|
| WO | WO 2010/069017 | 6/2010 |
| WO | WO 2019/133973 | 7/2019 |
| WO | WO 2019/211853 | 11/2019 |

OTHER PUBLICATIONS

European Search Report for European Application No. 20195796.6, dated Feb. 10, 2021, 8 pages.

\* cited by examiner (a)

(b)

(a)

(b)

(a)

(b)

| Models | LR | DL | DT | RF | GBT |
|---|---|---|---|---|---|
| Accuracy | 73.2 | 83.5 | 62.0 | 61.4 | 94.6 |
| Precision | 75.9 | 87.4 | 61.4 | 61.0 | 95.4 |
| Recall | 81.2 | 84.8 | 99.6 | 99.8 | 95.6 |

| Models | LR | DL | DT | RF | GBT |
|---|---|---|---|---|---|
| Accuracy | 83.6 | 94.7 | 78.5 | 76.2 | 98.5 |
| Precision | 88.0 | 95.6 | 76.7 | 74.5 | 99.3 |
| Recall | 88.4 | 96.8 | 99.2 | 99.8 | 98.5 |

APPARATUS AND METHOD FOR ASSESSING A CHARACTERISTIC OF A PLANT

The present application is based on and claims priority to United Kingdom Patent Application No. 1903652.4, filed on Mar. 18, 2019, the entire contents of which are incorporated herein by reference.

The present disclosure relates to a method and apparatus for assessing a characteristic of a plant. More particularly, but not exclusively, the present disclosure relates to a method and apparatus for assessing a characteristic of a plant based upon an electrical signal obtained from the plant using a machine learning technique.

It is known that electrical potential differences, or membrane potentials, are maintained across cell membranes in plants. However, it remains as a challenge to detect a health status of a plant with a reasonable-degree of confidence based upon an electrical signal obtained from the plant.

Thus, there is a need to provide an improved method and apparatus for accessing a characteristic of a plant based upon an electrical signal obtained from the plant.

According to a first aspect described herein, there is provided a method of assessing a characteristic of a plant, comprising: obtaining a training dataset, wherein the training dataset comprises first data characterising a first electrical signal obtained from a first plant during a first time period when a stressor is present in the first plant or in a growth environment of the first plant, second data characterising a second electrical signal obtained from the first plant during a second time period when a stressor is not present in the first plant or in the growth environment of the first plant, and third data indicative of a characteristic of the first plant during the first time period and a characteristic of the first plant during the second time period; training a machine learning model based upon the training dataset; obtaining a third electrical signal from a second plant; and assessing, using the trained machine learning model, a characteristic of the second plant based upon the third electrical signal.

By using a training dataset which comprises data characterising electrical signals obtained from a first plant to train a machine learning model, the trained machine learning model is able to assess a characteristic of a second plant based upon an electrical signal obtained from the second plant. In this way, the first aspect provides an effective way to assess an unknown characteristic of a plant based upon the electrical signal obtained therefrom, and allows a plant grower to take preventive measures before initial symptoms appear on the plant.

The first plant may be a single plant, and the first electrical signal may comprise electrical signals obtained from the plant at multiple different times, at multiple different parts of the plant, and/or when the plant is at multiple different locations. Alternatively, and more preferably, the first plant may comprise a group of plants, and the first electrical signal may comprise electrical signals obtained from each of the plants.

It will be appreciated that the expression "first data characterising a first electrical signal" means that the first data indicates a characteristic of the first electrical signal and is obtained by processing the first electrical signal. The expression "second data characterising a second electrical signal" has a similar meaning.

The stressor may be any factor which causes a change to the growth environment or the physiology of the first plant. The stressor typically causes the first plant to have a corresponding characteristic (e.g., light deficit/excess, water deficit/excess, nutrition deficit/excess, slow/fast metabolism, temperature deficit/excess, $CO_2$ deficit/excess, salt deficit/stress, insect infestation, pathogen presence where a pathogen may be a virus, fungus or bacteria, premature or delayed growth, flowering or fruit maturing etc.) associated with the nature of the stressor. Therefore, the characteristics of the first plant during the first and the second time periods are associated with the presence/absence of the stressor. Accordingly, the third data indicative of the characteristics of the first plant may be obtained based upon the presence/absence of the stressor within the growth environment without requiring further sensors. Alternatively, the third data may be obtained by monitoring a physiological marker of the first plant and/or an environmental condition of the first plant using a suitable sensor. The physiological marker (e.g., the leaf turgor pressure, stage of development of the plant, stem diameter, leaf fluorescence, leaf temperature, leaf colour, etc.) and/or the environmental condition (e.g., the ambient lighting condition, the ambient $CO_2$ level, the air temperature, the soil water content, etc.) directly and accurately indicate the characteristic of the first plant.

The machine learning model may be a regression model or a classification model (i.e., a classifier).

The first plant and the second plant may be of different plant varieties. Alternatively, but not necessarily, the first plant and the second plant may be of the same plant variety.

The first plant and the second plant may be the same plant. In particular, the first plant may be used at an earlier time for generating the training dataset to train a machine learning model, and it may be required to assess a characteristic of the same plant at a later time using the trained model. Alternatively, the first plant and the second plant are separate plants (which may be of the same plant variety or different plant varieties).

The first, second and third electrical signals may be signals in the time domain.

The terms "first" and "second" used the "first time period" and the "second time period" are merely labels to allow clear references to the time periods, and in no way implies temporal limitations to the time periods or the order in which they occur.

The third electrical signal may be obtained during periodic monitoring or continuous monitoring of the second plant.

Obtaining the training dataset may comprise: introducing the stressor to the first plant or the growth environment of the first plant; obtaining the first electrical signal from the first plant during the first time period when the stressor is being applied to the first plant or the growth environment of the first plant; and obtaining the second electrical signal from the first plant during the second time period when the stressor is not applied to the first plant or the growth environment of the first plant.

Obtaining the training dataset may further comprise: processing the first electrical signal to generate the first data; and processing the second electrical signal to generate the second data.

Processing the first electrical signal to generate the first data may comprise: performing signal conditioning on the first electrical signal.

Performing signal conditioning may comprise performing analogue and/or digital signal conditioning.

Said signal conditioning may comprise one or more of: amplifying, filtering, normalising, and/or down-sampling the first electrical signal.

Processing the first electrical signal to generate the first data may comprise: obtaining data samples from the first electrical signal at a predetermined sampling frequency.

At least one of the data samples may comprise a data segment obtained by applying a window function to the first electrical signal.

Applying a window function to the first electrical signal may comprise multiplying the window function and the first electrical signal. The window function may have non-zero values within a chosen time interval and may be zero-valued outside of the chosen time interval.

At least one of the data samples may comprise a plurality of data segments which are obtained by applying a plurality of window functions, respectively, to the first electrical signal, and the plurality of window functions have different time intervals from one another.

The window function or at least one of the window functions may have a time interval of less than 1 minute.

The window function or at east one of the window functions ay have a time interval of greater than 10 minutes.

Processing the first electrical signal to generate the first data may further comprise extracting at least one characterising feature from each data segment. The first data may comprise the at least one characterising feature.

The at least one characterising feature may be derived by means of statistical analysis or principal component analysis The at least one characterising feature may comprise one or more of: a generalised Hurst exponent; a skewness; an estimation of a power of a colour of noise; an interquartile range; a min or max value of coefficients obtained by a wavelet decomposition of a respective data segment.

Processing the first electrical signal to generate the first data may further comprise normalising the extracted at least one characterising feature.

Obtaining the training dataset may further comprise labelling the data samples using the third data.

The second data may be generated based upon the second electrical signal in the same way as the generation of the first data.

The training dataset may comprise a plurality of data entries, at least one of which comprising the at least one characterising feature extracted from a respective data sample and a label of the same data sample.

The machine learning model may comprise a classifier.

The classifier may be a gradient boosted tree model.

The stressor may be configured to affect a lighting condition of the first plant.

The stressor ay be configured to cause the first plant to have water stress.

Further or alternatively, the stressor may be configured to cause the first plant to be infested by insects, to be infected with a pathogen such as a virus, fungus or bacterium, to have $CO_2$ deficit, to have excess or insufficient nutrients, to have temperature stress (i.e., temperature being too hot or too cold for optimal growth), to have salt stress (e.g., salt level in the growth medium being too high or too low for optimal growth), and/or to prematurely cause or delay growth, flowering, or fruit maturing of the first plant.

Assessing a characteristic of the second plant based upon the third electrical signal may comprise: processing the third electrical signal to generate data characterising the third electrical signal; and providing the generated data as input data to the trained machine learning model.

The data characterising the third electrical signal may be generated based upon the third electrical signal in the same way as the generation of the first data.

The training dataset may further comprise environmental data characterising the growth environment of the first plant during the first and the second time periods.

The environmental data, the first data and the second data may form the input features of the training dataset. The third data may form the output features of the training dataset.

The method may further comprise: obtaining environmental data characterising a growth environment of the second plant; and assessing, using the trained machine learning model, the characteristic of the second plant based upon the third electrical signal and the environmental data characterising the growth environment of the second plant.

That is, the environmental data characterising the growth environment of the second plant may be provided as input data to the trained machine learning model.

The environmental data may comprise one or more of: data indicative of a light intensity in the growth environment, data indicative of soil water content of the growth environment, data indicative of a temperature (e.g., an air temperature) of the growth environment, data indicative of a humidity level of the growth environment. The environment data may be directly output by available sensors located in the growth environment, or may be processed sensor data.

The method may further comprise: generating plant data indicative of an assessment result of the characteristic of the second plant.

The plant data may be an output of the trained machine learning model, or may be generated based upon the output of the trained machine learning model.

The generated plant data may be used by a user to identify diseased plants within a growth environment (e.g., in a field).

The method may further comprise: sending an alert based upon the plant data.

Advantageously, the alert prompts a user to perform manual treatment to the second plant.

The method may further comprise: generating a plant control signal based upon the plant data, wherein the plant control signal is configured to change a growth environment of the second plant. Advantageously, the plant control signal automatically adjusts the growth environment of the second plant without requiring human intervention.

The plant control signal may be configured to adjust an operation of a nutrigation pump associated with the second plant. By adjusting an operation of a nutrigation pump, the throughput of the nutrigation pump may be increased or decreased. More specifically, the plant control signal may be configured to switch on or off the nutrigation pump.

Further or alternatively, the plant control signal may be configured to adjust the operation of at least one device, with the at least one device comprising one or more of a heater, a fan, a lighting, a pump which deliver a chemical substance to a growth medium of the second plant, and a pesticide pump. By adjusting the operation of the at least one device, the throughput and/or the output power of the device may be increased or decreased. More specifically, the plant control signal may be configured to switch on or off the at least one device. Further or alternatively, the plant control signal may be configured to alter a vent positon in the growth environment of the second plant.

According to a second aspect described herein, there is provided a computer program comprising computer readable instructions arranged to cause a processor to carry out a method according to the first aspect described here.

According to a third aspect described herein, there is provided a computer readable medium carrying a computer program according to the second aspect described herein.

According to a fourth aspect described herein, there is provided an apparatus for assessing a characteristic of a plant comprising: a processor arranged to carry out a method according to the first aspect described here; and a capture device configured to sense the first and second electrical signals from the first plant, and configured to sense the third electrical signal from the second plant.

The capture device may comprise a first electrode attached to the first/second plant, and a second electrode attached to a growth medium of the first/second plant or an alternative reference site (e.g., the stem or the root) of the first/second plant.

The first electrode and the second electrode may be attached to two different parts of the same plant, with the two different parts having different distances from the growth medium.

The first electrode may be a capture electrode attached to a first part of a plant. The second electrode may be a reference electrode attached to a second part of the same plant. The first part may be further away from the growth medium than the second part.

According to a fifth aspect described herein, there is provided an apparatus for assessing a characteristic of a plant comprising: a computer readable storage medium storing a machine learning model, wherein the machine learning model has been trained using a training dataset, wherein the training dataset comprises first data characterising a first electrical signal obtained from a first plant during a first time period when a stressor is present in the first plant or in a growth environment of the first plant, second data characterising a second electrical signal obtained from the first plant during a second time period when a stressor is not present in the first plant or in the growth environment of the first plant, and third data indicative of a characteristic of the first plant during the first time period and a characteristic of the first plant during the second time period; a capture device configured to sense a third electrical signal from a second plant; and a processor configured to assess a characteristic of the second plant based upon the machine learning model and the third electrical signal.

The computer readable storage medium may store a first machine learning model which has been trained by a first training dataset for assessing a first characteristic of a plant, and a second machine learning model which has been trained by a second training dataset for assessing a second different characteristic of a plant.

The first training dataset may further comprise first environmental data characterising a first condition of the growth environment, and the second training dataset may further comprise second environmental data characterising a second different condition of the growth environment.

The processor may select one of the first and second machine learning models for assessing a corresponding characteristic of the second plant.

The first/second machine learning model may be for assessing a nutrient insufficiency of a plant. The first/second environmental data of the first/second training dataset may comprise data indicative of a light intensity in the growth environment and data indicative of soil water content of the growth environment.

The first/second machine learning model may be for assessing whether a plant is infested by insects. The first/second environmental data of the first/second training dataset may comprise data indicative of a temperature (e.g., an air temperature) of the growth environment.

The first/second machine learning model may be for assessing whether a plant is infected with a pathogen (e.g., fungus). The first/second environmental data of the first/second training dataset may comprise data indicative of a humidity level of the growth environment.

The processor may receive environmental data characterising a condition of a growth environment of the second plant, and to assess a characteristic of the second plant based upon one of the stored machine learning models, the third electrical signal, and the received environmental data.

Alternatively, the computer readable storage medium may store a first machine learning model which has been trained by a first training dataset for assessing a first characteristic of a plant, and a second machine learning model which has been trained by a second training dataset for assessing the same first characteristic of a plant. The first training dataset may further comprise first environmental data characterising a first condition of the growth environment, and the second training dataset may further comprise second environmental data characterising a second different condition of the growth environment.

The processor may be configured to: receive environmental data characterising a particular condition of a growth environment of the second plant, determine that the particular condition is same as the first condition, and select the first machine learning model for assessing the first characteristic of the plant.

According to a sixth aspect described herein, there is provided a system comprising an apparatus according to the fifth aspect, and a plant control system configured to automatically change a growth environment of the second plant based upon the assessed characteristic of the second plant.

According to a seventh aspect described herein, there is provided a method of training a machine learning model for assessing a characteristic of a plant. The method comprises obtaining a training dataset, wherein the training dataset comprises first data characterising a first electrical signal obtained from a first plant during a first time period when a stressor is present in the first plant or in a growth environment of the first plant, second data characterising a second electrical signal obtained from the first plant during a second time period when a stressor is not present in the first plant or in the growth environment of the first plant, and third data indicative of a characteristic of the first plant during the first time period and a characteristic of the first plant during the second time period. The method further comprises training the machine learning model, using the training dataset, to assess a characteristic of a second plant based upon a third electrical signal obtained from the second plant.

There is also provided a computer readable medium comprising a trained machine learning model, wherein the model has been trained according to the method of the seventh aspect.

According to an eighth aspect described herein, there is provided a method of obtaining a training dataset for training a machine learning model for assessing a characteristic of a plant. The method comprises obtaining first data characterising a first electrical signal from a first plant during a first time period when a stressor is present in the first plant or in a growth environment of the first plant, obtaining second data characterising a second electrical signal from the first plant during a second time period when a stressor is not present in the first plant or in the growth environment of the first plant, and obtaining third data indicative of a characteristic of the first plant during the first time period and a characteristic of the first plant during the second time period. Said training dataset comprises said first data, said second data and said third data.

Where appropriate any of the optional features described above in relation to one of the aspects described herein may be applied to another one of the aspects described herein.

Embodiments are now described, by way of example only, with reference to the accompanying drawings, in which:

FIG. 1 schematically illustrates a plant health monitoring device in use with a plant;

FIG. 2 schematically illustrates the device shown in FIG. 1 in more detail;

In the figures, like parts are denoted by like reference numerals. It will be appreciated that the drawings are for illustration purposes only and are not drawn to scale.

Figure 1:
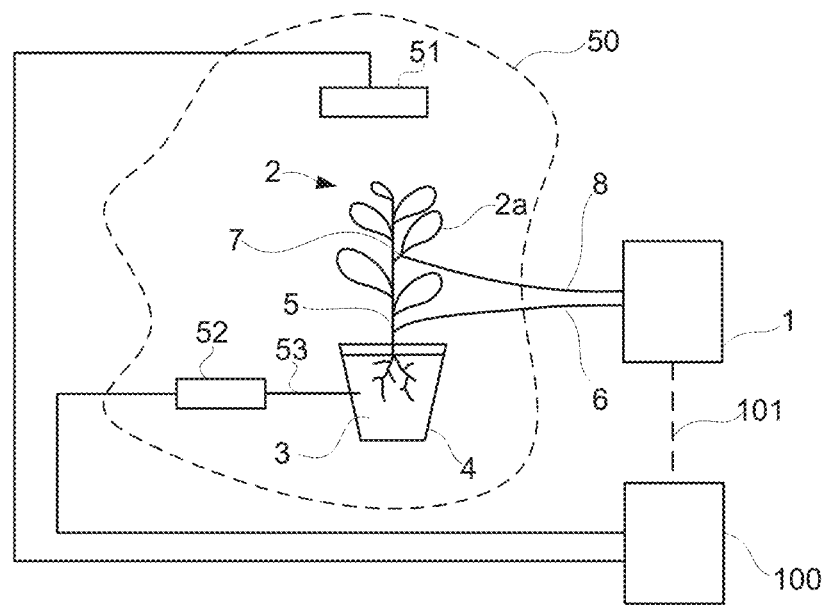

All living organisms have evolved complex signalling networks in response to the changing environment. The use of electrical signals is a universal way to transmit information rapidly. In animals, the bioelectrical activity in muscle (electromyogram), in heart (electrocardiogram) or in brain (electroencephalogram) can provide an indication of the health status of an animal. In plants, such practical use based on the bioelectrical activity is in its infancy and transposition of such technology could therefore, by analogy, provide an indication of the physiological status of a plant.

Plants have evolved several paths for long-range signal transmissions between cells, tissues and organs in order to adapt their physiology in response to a changing environment. This long-range signal communication can be triggered by biotic or abiotic stimuli that are sensed locally by a few cells and translated into mobile signals such as small molecules, peptides, second messengers, or phytohormones or mechanical vibrations. In contrast to the mobile signals, electrical signals are capable of transmitting information more rapidly over long distances. Electrical signals are known to regulate a wide variety of physiological processes, which may include growth, gas exchange, respiration, variation of photosynthesis and transpiration, modification of gene expression (e.g. protease inhibitor), plant motion, and expression of phytochemical like jasmonates, flowering, fruiting and maturation of fruits.

Most studies on electrical signals in plants have been carried out under laboratory-controlled conditions. For instance, researchers focused on the description of these signals, e.g., the amplitude, the frequency, the velocity, the distance and direction of signal propagation. Studies are now dedicated to identify the nature of the protein involved and how it is integrated in the complex signalling network to regulate physiological processes from the cellular level to the whole plant level. Approaches to study electrical signals include intracellular and extracellular measurements. The intracellular measurement can directly record the value of a potential of an individual cell membrane, while the extracellular measurement detects the spatiotemporal sum of the depolarization-repolarization process in a large group of cells. Amongst them, in plants, there are three different types of electrical signals: action potential (AP), variation potential (VP), and system potential or electric potential (SP or EP). AP is induced by non-damaging stimuli (e.g., cold, mechanical and electrical stimuli), whereas VP is induced by damaging stimuli (e.g., burning and cutting). Both of AP and VP are widespread signalling phenomena which can rapidly transmit information over long distances. SP is a sub-threshold response induced by changes in the environmental factors, e.g. soil, water, fertility, light, air temperature and humidity. However, it is quite often that mixed electrical potential waves are recorded, for instance, as results of overlapping APs, VPs and SPs from a variety of sources within the plant. This creates a complex web of systemic information in which several electrical signals may be layered on top of each other in time and space, and makes it hard to perform a conclusive signal analysis.

In the following description, instrumentation which allows the recording of aggregate bioelectrical activity from plants without the use of a Faraday cage is described, and a machine learning technique which predicts (or assesses) a characteristic of a plant based upon an electrical signal obtained from the plant is also described.

As shown in FIG. 1, a plant health monitoring device 1 is arranged to monitor the health of a plant 2. The plant 2 is grown in a growth medium 3 which is contained within a container 4. The growth medium 3 may be any suitable medium in which the plant 2 is able to grow. For example, the medium 3 may be soil, compost, water or the like. The growth medium 3 may also be referred to as a "substrate".

A reference electrode 5 is attached to or inserted into a stem of the plant 2, and is connected, by a lead 6, to the plant health monitoring device 1. A capture electrode 7 is attached to a petiole of a leaf 2a of the plant 2, and is connected, by a second lead 8, to the plant health monitoring device 1. Alternatively, the reference electrode 5 may be inserted into, or otherwise attached to, a portion of root of the plant 2, or into the growth medium 3. Attaching the reference electrode 5 to the stem/root of the plant 2 allows signal uncertainties coming from the medium 3 to be removed. For example, it has been found that variations in the moisture level of the medium 3 result in variations in the electrical signal sensed at the reference electrode 5. Therefore, it is more preferable to attach the reference electrode 5 to the stem/root of the plant 2 than to insert it into the medium 3.

In an example where both the reference electrode 5 and the capture electrode 7 are attached to the plant 2, it is preferable to attached the reference electrode 5 to a part of the plant 2 which is closer to the growth medium, and to attach the capture electrode 7 to another part of the plant 2 which is further away from the growth medium.

It will be appreciated that the capture electrode 7 may comprise a plurality of capture electrodes which can be attached to a plurality of plants 2 or multiple different parts of a single plant 2. Similarly, the reference electrode 5 may comprise one or more reference electrodes. In an exemplary set-up, the plant health monitoring device 1 has a plurality of reference electrodes 5 and a plurality of capture electrodes 7, and may be able to obtain electrical signals from eight different plants or from eight different parts of the same plant, at the same time.

FIG. 1 further shows that the plant 2 is within a growth environment 50. The growth environment 50 may be a growing chamber, a greenhouse or field. In an example, a light source 51 and an irrigation system 52 are provided within the growth environment 50. The irrigation system 52 is connected to the growth medium 3 via a tube 53. There is also provided a plant control device 100 in communication with the plant health monitor device 1 via a communication link 101. The plant health monitoring device 1 obtains electrical signals from the plant 2, and the electrical signals are used to assess a characteristic of the plant 2 by the device 1 or another device connected to the device 1. The communication link 101 may be a direct or an indirect communication link (e.g., via another device). Based upon the assessed characteristic of the plant 2, the plant control device 100 automatically controls the environmental conditions in which the plant 2 is grown, by, for example, controlling the light source 51 and the irrigation system 52. The plant control device 100, the light source 51 and the irrigation system 52 thus collectively provide a plant control system. It will, of course, be appreciated that various combinations of environmental conditions may be controlled by the plant control system. Indeed, other aspects of the plant's environment may be controlled than those described above. For example, in addition to (or instead of) one or more of the light source 51 and the irrigation system 52, the plant control system may comprise a device which applies fungicide or insecticide to the plant 2, a device which controls the humidity within the environment 50, a nutrigation pump or other device which delivers nutrition to the plant 2, a pump which delivers chemical substance (e.g., salt) to the growth medium 3, a heater, a fan, and/or a vent, etc. The plant control device 100 may be configured to automatically control any of the devices within the plant control system, so as to control various environment conditions of the growth environment 50.

Figure 2:
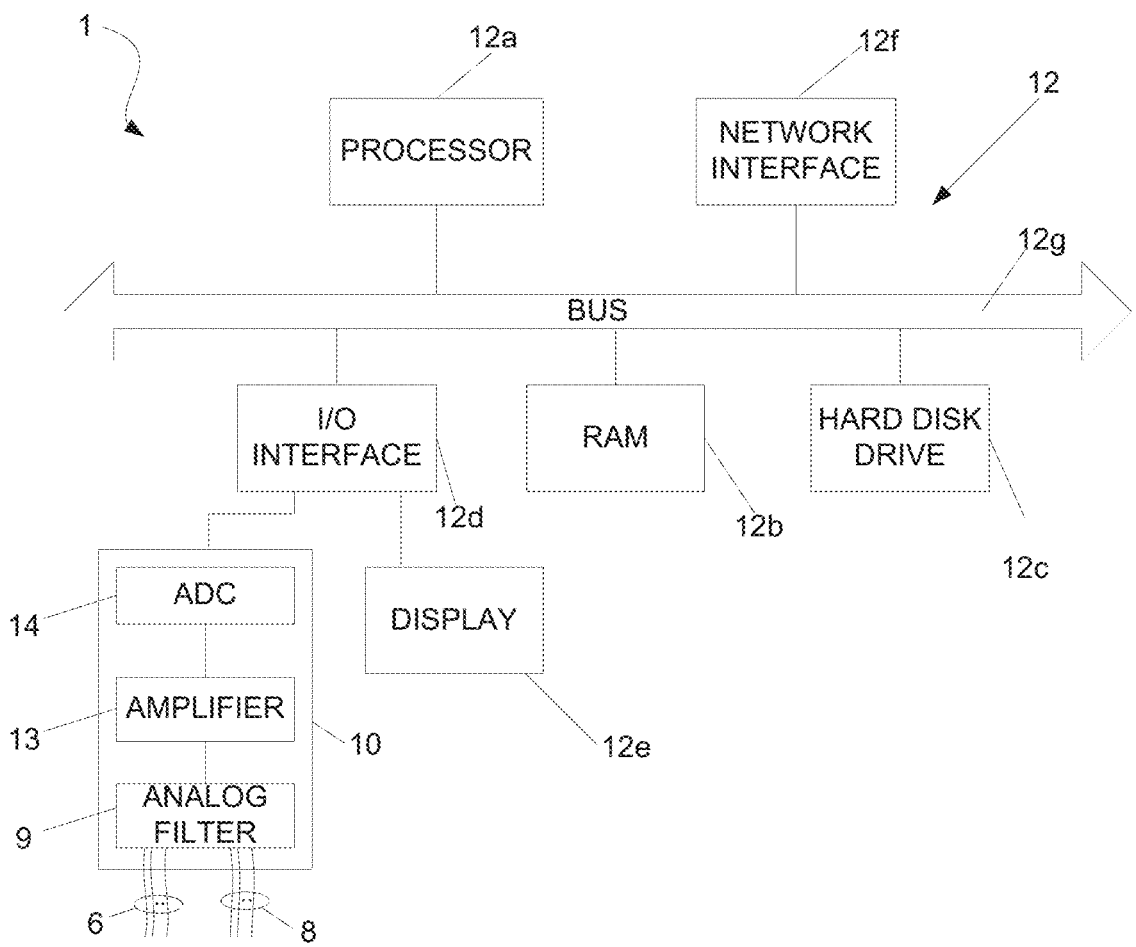

As shown in more detail in FIG. 2, the plant health monitoring device 1 comprises a data acquisition module 10 and a controller 12. The leads 6, 8 are connected to inputs of the data acquisition module 10. The data acquisition module 10 measures voltage potential differences present between each pair of the electrodes 5, 7 in the plant 2. Electrical signals may be recorded in mV level as a function of time and may be recorded at a rate of 240 Hz (i.e., 240 samples per second) by the data acquisition module 10. The recording frequency of the data acquisition module 10 may, for example, be any value between 1 Hz to 10 KHz.

In more detail, the data acquisition module 10 comprises an analog filter 9, an amplifier 13, and an analog-to-digital converter (ADC) 14. The analog filter 9 may be a low-pass filter. In an example, the analog filter 9 may be a DC-30 Hz filter with a gentle 6 dB/octave roll off. Such a filter is useful for minimal ringing so that the transient waveforms have minimal distortion in the time domain. The amplifier 13 may be an analog, non-switching, instrumentation amplifier and may provide an amplification factor between 0 and 100. In an example, the amplifier 13 provides an amplification factor of 4.

The ADC 14 may be of a Successive Approximation Register (SAR) design. In an example, the ADC 14 may be a 18-bit SAR ADC capable of processing 100K samples per second. In particular, the ADC 14 has a sample-and-hold input and may return a full 18-bit signed value over a +/−2.048V range for each input. The ADC 14 may be implemented using ADS8777 ADC made by Texas Instruments.

The controller 12 comprises a processor 12a which is configured to read and execute instructions stored in a volatile memory 12b which takes the form of a random access memory. The volatile memory 12b stores instructions for execution by the processor 12a and data used by those instructions. For example, in use, the data acquired by the data acquisition module 10 may be stored in the volatile memory 12b.

The controller 12 further comprises non-volatile storage in the form of a hard disc drive 12c. The data acquired by the data acquisition module 10 may be stored on the hard disc drive 12c. The controller 12 further comprises an I/O interface 12d to which are connected data capture and peripheral devices used in connection with the controller 12. A display 12e is connected to the I/O interface 12d to display output from the controller 12. The display 12e may, for example, display a representation of the data acquired by the data acquisition module 10. The display 12e may be provided locally to the plant health monitoring device 1 (e.g. as a screen), or remotely from the plant health monitoring device 1. For example, a display associated with a separate device (e.g. a mobile computing device) may be used as a display for the plant health monitoring device 1. Additionally, the display 12e may display images generated by processing of the data acquired by the data acquisition module 10. Additionally, a touchscreen associated with the display 12e may operate as a user input device, so as to allow a user to interact with the controller 12. Alternatively or additionally, separate input devices may be also connected to the I/O interface 12d. A network interface 12f allows the controller 12 to be connected to an appropriate computer network so as to receive and transmit data from and to other computing devices. The processor 12a, volatile memory 12b, hard disc drive 12c, I/O interface 12d, and network interface 12f, are connected together by a bus 12g.

In addition to the peripheral devices described above being connected to the I/O interface 12d, the output of the data acquisition module 10 is also connected to the I/O interface 12d. By virtue of these connections, potential differences sensed at the electrodes 5, 7 can be processed and converted to a digital signal by the data acquisition module 10 and subsequently processed by the processor 12a and stored in the hard disc drive 12c.

The controller 12 may be connected to an external computer/server via the network interface 12f. In that case, the external computer/service may further process the digitalised signals obtained by the controller 12. In an example, the digitalised signals may be extracted and processed using a data processing software by the external computer/server. Further or alternatively, the controller 12 may be connected to a single board computer via the network interface 12f, such that the digitalised signals obtained by the controller are collected into the single board computer.

The controller 12 may comprise a microcontroller to which the output of the ADC 14 is fed. In an example, the controller 12 may comprise a single board computer which provides a STM32F103 microcontroller. The STM32F103 microcontroller uses the ARM M3 processor design and runs at 72 MHz. The STM32F103 microcontroller also provides USB connectivity.

In general, due to natural and man-made terrestrial electromagnetic noise as well as the low-voltage level of the potential variations produced by the plant 2, a Faraday cage is typically used to surround the plant 2, the leads 6, 8 and the device 1 when electrical signals are obtained from the plant 2. The Faraday cage acts to shield the plant 2, the leads 6, 8 and the device 1 from external sources of electromagnetic radiation.

In order to allow for operating the device 1 outside of a Faraday cage, one or more of the following design implementations may be made to the device 1.

Electrostatic discharge (ESD) protection circuits may be provided to the inputs of the data acquisition module 10. The pre-ADC analog filter 9 may be designed for minimal overshoot and ringing so that the transient waveforms have minimal distortion in the time domain. As described above, in an example, the analog filter may be a DC-30 Hz filter with a gentle 6 dB/octave roll off. An ultra-low input bias current instrumentation amplifier may be selected for use as the amplifier 13. The analog filter 9, the amplifier 13, and the ADC 14 may be typically implemented on a printed circuit board (PCB). In that case, the PCB may be designed such that it includes multiple (e.g., at least two) ground planes connected to one another by a plurality of vias, thereby ensuring short electrical ground current return paths. Further, the ADC 14 may be designed such that the analog input signal to the ADC 14 is oversampled (i.e., sampled at a sampling rate significantly higher than the Nyquist rate), and the output signal of the ADC 14 is then processed through a digital filter and a decimator. Moreover, a digital notch filter, such as a 50 Hz/100 Hz or 60 Hz/120 Hz digital notch filter may be included to process the output signal of the ADC 14.

In addition to the above described design implementations to the device 1, the leads 6, 8 may be coaxial cables which are arranged to connect each of the electrodes 5, 7 to the plant health monitoring device 1. The coaxial cables may be useful for shielding the leads 6, 8 from external sources of electromagnetic radiation.

For the ease of description, the coaxial cable connected to the reference electrode 5 is referred to as a "reference cable" and the coaxial cable connected to the capture electrode 7 is referred to as a "capture cable". A coaxial cable typically comprises an inner conductor surrounded by a tubular insulating layer, further surrounded by a tubular outer conducting shield. The inner conductors of the coaxial cables act as the leads 6, 8 and are used to transfer signals sensed by the electrodes 5, 7 to the plant health monitoring device 1. The outer conducting shields of the coaxial cables act as the EM shield 9 to shield electromagnetic interference on the signals sensed by the electrodes 5, 7.

The coaxial cable has a capacitance between its inner conductor and its outer conducting shield. The capacitance of the coaxial cable may distort the signals sensed by the electrodes 5, 7. Thus, to compensate for the capacitance of the capture coaxial cable, a compensation circuit may be provided with the capture cable.

In more detail, the capture coaxial cable may be electrically connected to the capture electrode 7 via its inner conductor alone. The inner conductor of the capture cable provides an electrical signal sensed by the capture electrode 7 to the plant health monitoring device 1. The compensation circuit includes a buffer circuit with an amplification factor of '1' for the capture cable. The buffer circuit receives a voltage signal from the inner conductor of the capture cable and outputs a voltage signal to drive the outer conducting shield of the same cable. In this way, the voltage difference between the inner conductor and the outer conducting shield of the capture coaxial cable is maintained at substantially 0 Volt by the buffer circuit. Accordingly, the capacitance of the capture cable does not charge or discharge based upon signal level fluctuations, and the distortion caused by the capacitance of the capture cable to the signals sensed by the electrodes 5, 7 may be reduced to a negligible level. The buffer circuit may, for example, take the form of a voltage follower. The voltage follower may be an op-amp circuit which has a negative feedback and a voltage gain of '1'.

The reference cable may be electrically connected to the reference electrode 5 via both of its inner conductor and outer conducting shield. That is, the inner core and the outer conducting shield of the reference cable may be electrically coupled together with a voltage difference of substantially 0 Volt. The outer conducting shield is driven with a voltage of 0 Volt (i.e. ground), to provide a low impedance path for channeling any interference to the ground. The inner conductor of the reference cable, which is also at a voltage of substantially 0 Volt, provides an electrical signal to the plant health monitoring device 1. In this configuration, the reference cable does not require a compensation circuit to compensate for the capacitance of the cable.

Alternatively, the reference cable may be connected to the reference electrode 5 via its inner conductor alone, and accordingly may have its own compensation circuit as described above with reference to the capture cable. In either of these two configurations for the reference cable, the voltage difference between the inner core and the outer conducting shield of the reference cable is substantially zero. Accordingly, the capacitance of the reference cable does charge or discharge during signal acquisition, so its effect to the electrical signal sensed by the electrodes 5, 7 may be considered to be insignificant. Thus, transient distortions of the electrical signals obtained from the reference electrode 5 as a result of cable capacitance may be considered to be insignificant.

The plant health monitoring device 1 allows either short-term or long-term monitoring of electrical signals obtained from plants. Short-term or live recordings of electrical signals may be followed with wireless devices connected with the controller 12 via the network interface 12$f$. Long-term monitoring of electrical signals obtained from plants using the device 1 is described below with reference to FIGS. 3 and 4.

By way of example, the device 1 is used to perform long-term monitoring of electrical signals obtained from tomato plants. The tomato plants are grown in greenhouses in either Rockwool mineral substrate or an organic substrate composed of compost of bark (35%), a peat substitute (30%). Coco peat (20%) and topsoil 15%. It will be appreciated other suitable substrates may be used for the plants. An organic nutrient solution based on biogas digestate may be provided to the tomato plants as fertiliser.

For crop production in greenhouses, the climate management is crucial as well as the control of irrigation. Control of water uptake and the maintenance of water status are key for the survival and optimal growth of plants. Environmental factors such as radiation, air temperature, rainfall, and humidity have a high impact on plant water balance. Hence, plants require a coordinated and timely response in above-ground and below-ground organs to cope with the changing need to take up and preserve water.

In order to monitor the plants' responses to changing watering conditions, a group B of tomato plants was submitted to varying irrigation regimes, and a group A of tomato plants was placed under full irrigation all the time. Each group has more than 10 plants. In particular, the group-B plants were placed under full irrigation (corresponding to soil water content of 35% by volume) during a period Q1 of two and a half days. Subsequently the group-B plants were submitted to half of the irrigation during a period Q2 of three and a half days leading to a drop of soil water content that is maintained at around 25% by volume. During a subsequent period of Q3 of 36 hours, irrigation was completely stopped for the group-B plants and the soil dried out to a soil water content of 18% by volume. After the period Q3, the group-B plants were again placed under full irrigation (in a period Q4). The periods for the irrigation regimes are shown in each of FIGS. 3(a) and 3(b). In each of FIGS. 3(a) and 3(b), the vertical arrow indicates the beginning of the period Q4 when the group-B plants were watered again after drought condition. The soil water content may be measured by any suitable soil water sensor, such as, for example, the WET sensor made by Delta-T Devices Ltd, Cambridge, UK. The soil water sensor may also measure other parameters of the substrate, such as, the temperature and/or the electrical conductivity of the substrate. The soil water sensor may conduct three measurements per day.

A leaf turgor sensor was mounted onto the group-A plants and the group-B plants to detect the leaf turgor pressure of the plants. It was understood that the leaf turgor pressure may be useful to reflect the health state of the plants. The leaf turgor sensor may be a commercialized Yara Water-Sensor made by Yara International ASA. The Yara water-sensor measures the relative changes in the leaf's turgor pressure of a plant, and may record the relative changes at a rate of 1 sample per minute. FIG. 3(a) illustrates the mean turgor pressure measured from each of the group-A plants (i.e., curve 16) and the mean turgor pressure measured from each of the group-B plants (i.e., curve 18), with reference to the left Y axis. FIG. 3(a) further illustrates the variations of the soil water content (i.e., curve 20) of the group-B plants with reference to the right Y axis.

For comparison, the plant health monitoring device 1 as described above was attached to the group-A plants and the group-B plants to detect the electrical signals of the plants. FIG. 3(b) illustrates the mean electrical signal measured from each of the group-A plants (i.e., curve 22) and the mean electrical signal measured from each of the group-B plants (i.e., curve 24), with reference to the left Y axis. FIG. 3(b) further illustrates the variations of the soil water content (i.e., curve 20) of the group-B plants with reference to the right Y axis.

As shown in FIG. 3(a), the leaf turgor pressure shows a daily variation with a minimum leaf turgor during the night and a maximum reached during the day. To better characterize this daily variation, the leaf turgor signals were normalised and split into 24-hour cycles as shown in FIG. 4(a). In FIG. 4(a), the curve 25 shows the leaf turgor signal of plants which were under full irrigation, the curve 26 shows the leaf turgor signal of plants which were under half irrigation and the curve 27 shows the leaf turgor signal of plants which were under no irrigation. As shown in FIG. 4(a), in water deficit regime (e.g., during the periods Q2 and Q3), the daily variation of leaf turgor is modified with a drop of turgor during the day. The more the soil water content diminishes, the more the leaf turgor drops until the signal is lost. As shown in FIG. 3(a), the leaf turgor signal is not recovered even after the irrigation had been restored during the period Q4. This indicates a limit of the leaf turgor sensor for indicating the plant status.

Turning to FIG. 3(b), as a general observation, the electrical signals obtained from the plants A and B present cyclic pattern with a minimum during late night/early morning and a maximum during the middle of the day (i.e., solar noon at about 14 h). To better characterize this daily rhythm, the electrical signals were normalised and split into 24-hours cycles as shown in FIG. 4(b). In FIG. 4(a), the curve 28 shows the electrical signal of plants which were under full irrigation, the curve 29 shows the electrical signal of plants which were under half irrigation and the curve 30 shows the electrical signal of plants which were under no irrigation. As shown in FIG. 4(b), when the group-B plants were under full irrigation, an initial slight peak is observed at dawn and during the first hours of the days. It was followed by a long-lasting peak with a higher amplitude in the middle of the day. This daily rhythm is similar to that recorded under controlled conditions on avocadoes or cucumber and strongly suggests an effect of the biological rhythm.

With further reference to FIG. 3(b), the variations of the electrical signals obtained from the group-B plants (as shown in curve 24) show a progressive hyperpolarization during the half-irrigation regime (i.e., Q2), because the centreline of the electrical signals kept decreasing during the period Q2. In general, hyperpolarization is a change in a cell's membrane potential that makes it more negative. The resulting electrical signal could be positive or negative as it is being used to communicate the state of stress throughout the plant. At the beginning of the period Q4, a strong transient hyperpolarization is evoked with an amplitude of −32 mV. During the period Q4, after the variation of the electrical signals slowly repolarizes, the electrical signals show the same daily rhythm as in the beginning.

Figure 3:
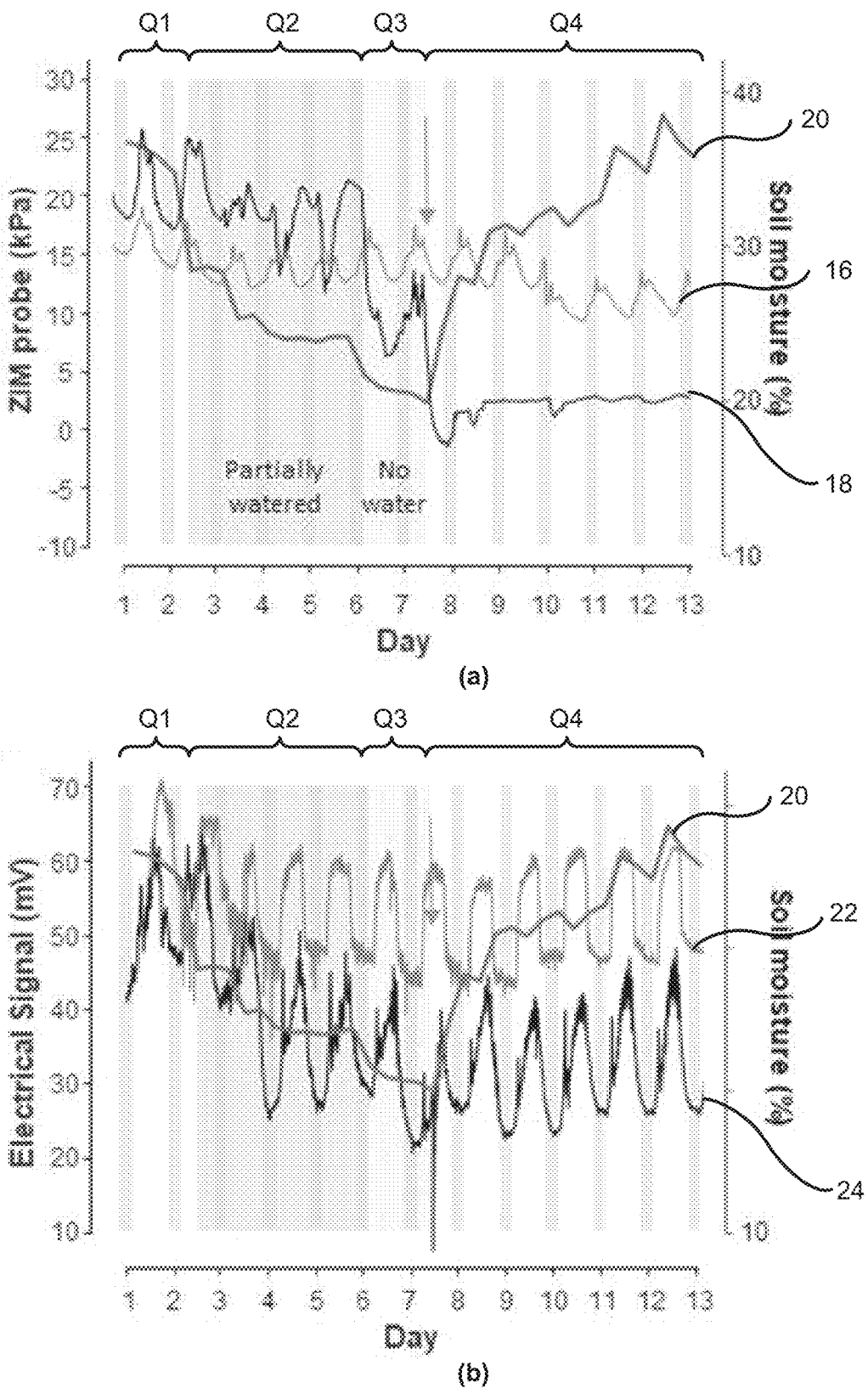
FIG. 3 illustrates (a) turgor pressure variation and (b) electric signal variation on plants in response to water deficit.
Figure 4:
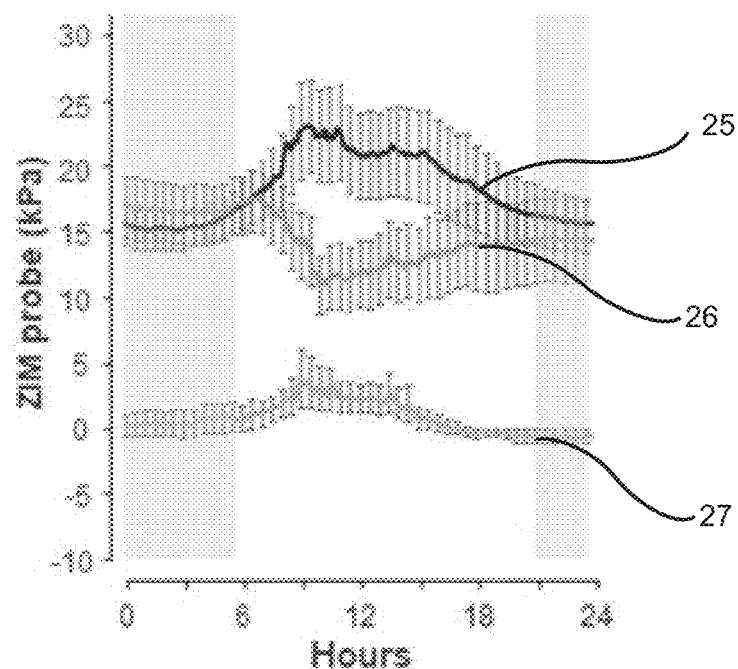
FIG. 4 illustrates (a) turgor pressure variation and (b) electric signal variation on plants during full irrigation, half irrigation and no irrigation.
Figure 4:
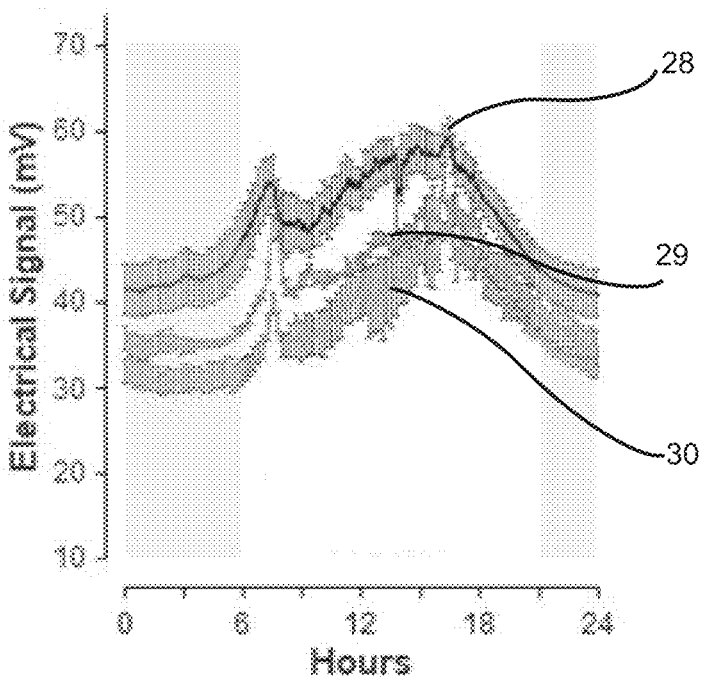

The results presented by FIGS. 3 and 4 demonstrate that in severe conditions of water deficit, monitoring the electrical variations is more efficient than monitoring the leaf turgor for the recovery phase. The results further demonstrate that the electrical signals obtained from plants by the device 1 contain useful information indicative of the water stress conditions of the plants.

Daily electrical variations have been reported on different plant species such as maize, prunes or avocado. Therefore it will be appreciated that the device 1 can be used to monitor electrical signals (either in short-term or in long-term) obtained from various species of plants which are in no way limited to tomato plants.

Figure 5:
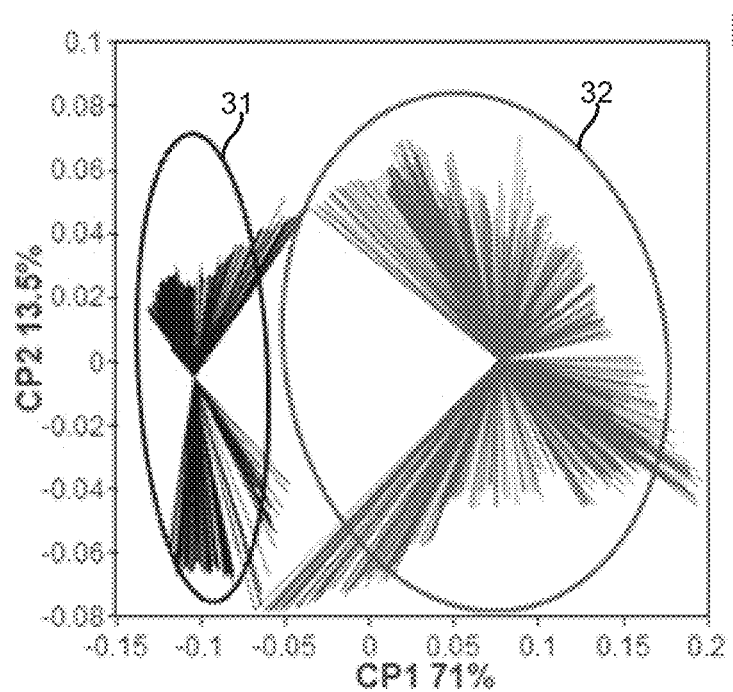
FIGS. 5 and 6 illustrate the results of principal component analysis performed on the raw data of the electrical signals obtained from plants.
Figure 5:
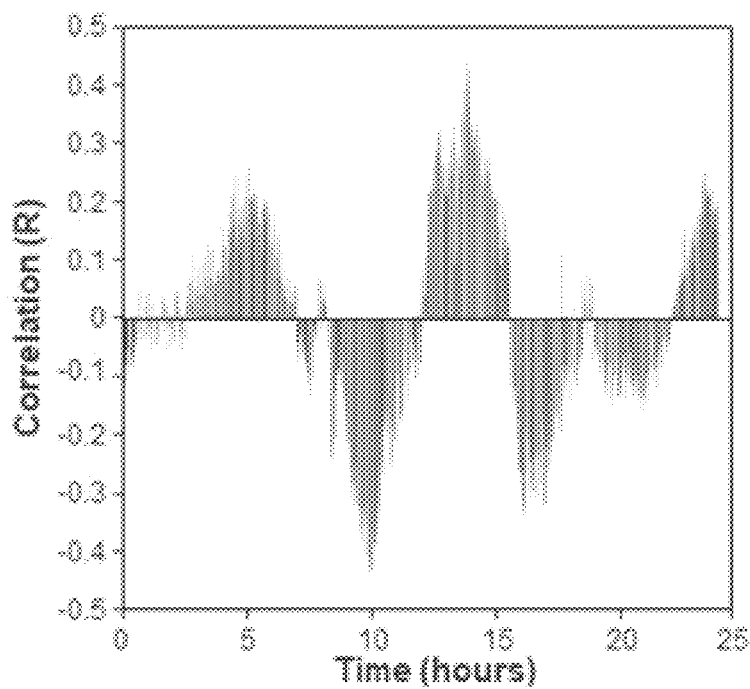
Figure 6:
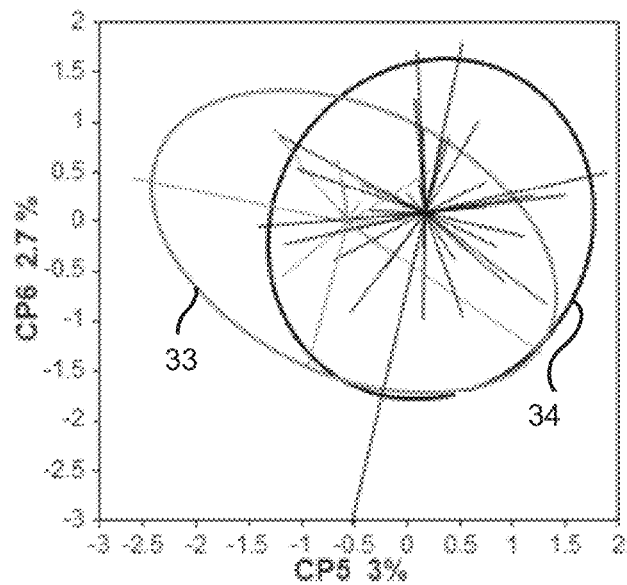
Figure 6:
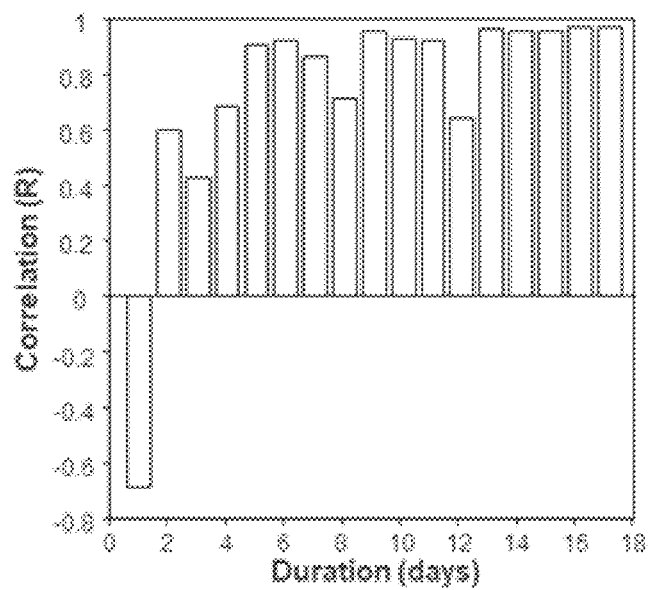

With reference to FIGS. 5 and 6, the raw data of the electrical signals obtained from plants have been analysed using principal component analysis (PCA) in order to explore the variability of the electrical signals with respect to night/day periods and the irrigation status.

By way of example, the device 1 is used to obtain electrical signals from a tomato plant described above. It will of course be appreciated that different species of plants may be used.

In order to explore the variability with respect to night/day periods, the obtained electrical signals have been arranged in a matrix $X_{n,p}$ with p being the number of days in which the plant was monitored and n being the number of data samples recorded each day. In an example, p is equal to 17, and the data samples are recorded at a frequency of 1 sample per minute, thus making n equal to 1440. Each data item in the matrix $X_{n,p}$ represents the amplitude of the obtained electrical signal.

After performing the PCA on the matrix $X_{n,p}$, the obtained factorial map of the PCA according to the first two factor scores is shown in FIG. 5(a). The X axis of FIG. 5(a) represents the first principal component (CP1) which accounts for 71% of the overall variability of the data. The Y axis of FIG. 5(a) represents the second principal component (CP2) which accounts for 13.5% of the overall variability of the data. FIG. 5(a) shows that the day and night periods can be separated into two distinct groups. In FIG. 5(a), the data group 31 corresponds to the night period, and the data group 32 corresponds to the day period. This means that some portions of the raw electrical signals contain relevant information for measuring a different behaviour of the plant between the periods of day and night. In order to determine at what time of day the relevant information contained in the electrical signals is located, the correlation between the factorial coordinates of the first principal component and the raw data of the electrical signals was calculated for each data sample recorded within a day. The results of the calculated correlation are shown in FIG. 5(b). With reference to FIG. 5(b), the strongest correlations are at around 2 pm (solar noon) and to a lesser extent at around 10 am and 4 pm.

In order to explore the variability with respect to the irrigation status of the plant, the obtained electrical signals have been arranged in a matrix $Z_{n,p}$ with n being the number of days in which the plant was monitored and p being the number of data samples recorded each day. In an example, n is equal to 17, and the data samples are recorded at a frequency of 1 sample per minute, thus making p equal to 1440. Each data item in the matrix $Z_{n,p}$ represents the amplitude of the obtained electrical signal. In some of the monitored days, the plant was placed under optimal full irrigation while in the other days, the plant was in conditions of water deficit. The irrigation status of the plant within the monitored 17 days results from the irrigation scheme imposed on the plant and may be manually recorded in a diary. Alternatively, the irrigation status of the plant may be automatically measured using a soil water sensor described above. Thus, the irrigation status of the plant within the monitored 17 days is known.

After performing the PCA on the matrix the obtained factorial map of the PCA according to the fifth and sixth principle components is shown in FIG. 6(a). The X axis of FIG. 6(a) represents the fifth principal component (CP5) which accounts for 3% of the overall variability of the data. The Y axis of FIG. 6(a) represents the sixth principal component (CP6) which accounts for 2.7% of the overall variability of the data. The factorial map shown in FIG. 6(a) allows for obtaining two different groups that are overlapped. In FIG. 6(a), the data group 33 corresponds to the water deficit (i.e., water-stress) state, and the data group 34 corresponds to the full irrigation (i.e., water-comfort) state. The correlation between the factorial coordinates of the fifth principal component and the raw data of the electrical signals was calculated for each of the monitored days. The results of the calculated correlation are shown in FIG. 6(b). With reference to FIG. 6(b), almost all of the monitored days appear important and are able to give information to distinguish the stressed plant from the non-stressed plant. However, the overall variability of the data that explains the difference between water-comfort and water-stress is relatively small when the electrical signals are used in the raw configuration. Thus, in order to better extract information related to water stress from the electrical signals, more sophisticated processing to the electrical signals may be useful.

Figures 7, 8, 9:
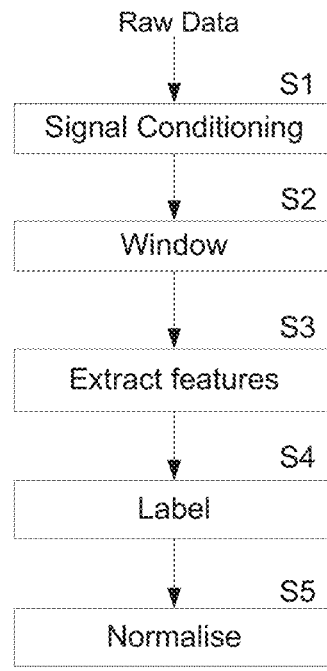
FIG. 7 is a flowchart showing processing steps carried out to pre-process the electrical signals obtained from plants before the application of a machine learning technique.
FIG. 8 shows the performances of five classifier models with respect to classification of lighting conditions of plants.
FIG. 9 shows the performances of five classifier models with respect to classification of water stress statuses of plants.

FIG. 7 illustrates processing steps carried out to the raw data of the electrical signals obtained from plants, in order to reduce the data dimensionality and to extract meaningful information from the electrical signals. The raw data of the electrical signals may be obtained by the leads 6, 8 of the device 1 as described above. In an example, the raw data comprises data obtained from five different tomato plants, and each plant has been monitored continuously for two weeks by the device 1.

During the two-week monitoring time for each plant, the lighting condition for the plants is recorded. The lighting condition may be manually recorded, or alternatively may be automatically detected and recorded by a light sensor installed in a growth environment (e.g., the growth environment 50) in which the plants grow. Further, during the two-week monitoring time, the level of irrigation (e.g., 100%, 20% and 0%) for each plant has been varied purposely according to a predetermined schedule. Data indicating the variations of the level of irrigation may be kept in a record. It is recognised that in general, the plants are in water stress three hours after the irrigation is reduced or removed. Thus, the water stress statuses of the plants during the two-week monitoring time may be derived based upon the level of irrigation. Alternatively or in addition, the water stress statuses of the plants may be characterised and recorded by using a leaf turgor sensor as described above. In general, the lighting condition record and the water-stress-status record of the plants indicate the lighting condition and the water stress statuses of the plants, respectively, within the entire two-week monitoring time.

The processing of FIG. 7 may also be referred to as "data pre-processing". The data pre-processing may be carried out by the device 1, and/or an external computer/server which is connected to the device 1 via the network interface 12f. Alternatively, the raw data may be stored in the device 1 for subsequent processing by any suitable device(s). With reference to FIG. 7, the data preprocessing comprises five phases: signal conditioning (step S1), windowing (step S2), extracting features (step S3), labeling (step S4), and normalising (step S5).

At Step S1, signal conditioning is performed on the raw data of the electrical signals obtained from plants. Various types of signal conditioning may be used (both in the analogue and digital domains) to remove any unwanted signal components, or to enhance other signal components as required. In particular, the signal conditioning may comprise one or more of: amplifying, filtering, normalising, and/or down-sampling the first electrical signal. It will be appreciated that the signal conditioning may be partly performed by the hardware provided in the data acquisition model 10 of the device 1, and/or suitable device(s) external to the device 1. For instance, the analog filter 9 of the data acquisition model 10 performs signal conditioning in the analogue domain to remove unwanted frequency components, and the amplifier 13 of the data acquisition model 10 performs signal conditioning in the analogue domain by amplifying the sensed signals to a level which is suitable for digitisation. Further, as described above, a digital filter and a decimator may be provided to perform signal conditioning on the digitised signal output by the ADC 14, by performing digital filtering and decimation (i.e., down-sampling). The digital filter may be a digital notch filter, such as a 50 Hz/100 Hz or 60 Hz/120 Hz digital notch filter. Moreover, the signals obtained from various plants or various parts of the same plant may be normalised at step S1. It will be appreciated, however, that the use of any particular signal conditioning device is optional. Alternatively signal artefacts contained within the raw data may be removed manually or automatically. After step S1, conditioned data is obtained.

At step S2, a data sample is taken from the conditioned data periodically (e.g., at a rate of one sample per every 5 minutes). Each data sample includes at least one data segment obtained by applying a window function to the raw data. The window function has non-zero values within a chosen time interval and is zero-valued outside of the chosen time interval. Thus, by multiplying the window function and the raw data, a data segment in the time domain is obtained.

In the event that each data sample includes multiple data segments, multiple window functions with different time intervals (i.e., window sizes) are applied to the conditioned data separately to obtain the multiple data segments. In one example, the time intervals of the multiple window functions may start at the same time but end at different times. In another example, the time intervals of the multiple window functions may start at different times but end at the same time. In an example, each data sample includes seven data segments which are obtained by applying seven different window functions to the raw data. The time intervals of the seven window functions may be 15 seconds, 30 seconds, 1 minute, 2 minutes, 5 minutes, 10 minutes and 30 minutes, respectively. Thus, the data segments included within one data sample have different temporal lengths (i.e., corresponding to the window sizes). Depending upon the particular window functions being used, it would be appreciated that the beginning and/or the end of the conditioned electrical signals may be discarded for the purpose of obtaining data samples at step S2.

It will be understood that in the event that the maximum window size of the window function(s) used is 30 minutes, if data samples are taken from the conditioned data at a rate of greater than 1 sample per 30 minutes (e.g., a sample per 5 minutes), the data segments included within neighbouring data samples may be partially overlapping in time.

At step S3, each data segment obtained at step S2 is processed to extract characterising features of the data segment. In an example, 26 characterising features are extracted from each data segment. The 26 features may include: simple statistical features (i.e., min, max, mean, variance, skewness, kurtosis and interquartile range), Hjorth parameters (i.e., mobility and complexity), generalized Hurst exponent, wavelet entropy (i.e., Shannon and logarithmic) and the estimation of the power of each color of noise (i.e., white, pink, brown, blue and purple) contained in the respective data segment. Further, wavelet decomposition may be performed on each data segment to more than one level, and simple statistical features (min, max, average) of the coefficients extracted at at least one level of the wavelet decomposition may be calculated. In an example, data processing software (e.g., Matlab) may be employed to perform wavelet decomposition to eight levels on each data segment, and the coefficients at three of the eight levels, e.g., level-1 (high frequencies), level-4 (medium frequencies) and level-8 (low frequencies), may be extracted. The min, max and average values of the coefficients (e.g., the approximation and/or the detail coefficients) extracted at each of the three levels are then calculated, thereby resulting in 9 characterising features in total. The wavelet decomposition is a multi-level discrete wavelet transform and may be implemented using the "wavedec" function in Matlab software. Performing wavelet decomposition to multiple levels generally requires multiple levels of wavelet analyses. When each data sample includes seven data segments of different window sizes, it will be understood that each sample has 26*7 (182) characterising features in total.

At step S4, each data sample is labelled with a corresponding lighting condition and a corresponding water stress status of the respective plant. The labelling is based upon the lighting condition record of the plants and the water-stress-status record of the plants as described above. The corresponding lighting condition forms Class 1 label and may indicate "day" or "night". The corresponding water stress status forms Class 2 label and may indicate "normal" or "water stressed".

At step S5, normalisation is applied to the extracted characterising features of the data samples obtained across different plants, to compensate for the inter-plant variability in the extracted features. More precisely, the values of each feature vector may be transformed in the interval between 0 and 1 using Equation (1) below:

$$X_{nf} = \frac{X_f - X_{f,min}}{X_{f,max} - X_{f,min}} \quad (1)$$

where $x_f$ and $x_{nf}$ are the raw feature vector generated at step S3 and the normalized feature vector, respectively, while $x_{f,min}$ is the feature vector minimum and $x_{f,max}$ is the feature vector maximum.

After the data preprocessing of FIG. 7 is performed, each data sample obtained at step S2 provides one data entry, which includes the extracted characterising features (i.e., input features) of the data sample obtained at step S3 and the corresponding labels (i.e., output features) of the data sample obtained at step S4. In an example, a dataset of 24246 data entries are obtained after the data preprocessing of FIG. 7. 60.3% of the data entries are labelled as "day" under the Class 1 label, and 39.7% are labelled as "night" under the Class 1 label. With regard to the Class 2 label, 30.8% of the data entries are labelled as "water stressed" and 69.2% are labelled as "normal".

The dataset obtained by the data preprocessing of FIG. 7 are then split into a learning dataset (also referred to as a "training dataset") and a validation dataset. The learning dataset may take up to 80% of the whole dataset, and the validation dataset may take up to 20% of the whole dataset.

The learning dataset is provided to a classifier to train the classifier. A classifier is a supervised machining learning algorithm which approximates a mapping function (F) from input variables (X) to discrete output variables (Y). The input variables (X) may correspond to the extracted characterising features of each data sample. The output variables (Y) may correspond to the Class 1 and/or Class 2 labels of the data samples. Each of the input variables has a corresponding weight, which indicates the strength of the input variable in determining an output variable. Training a classifier basically means calibrating all of the weights. After the classifier is trained, the validation dataset is used to test the performance of the trained classifier. For example, the trained classifier generates an output value based upon the input features of a data entry within the validation set, and the generated output value is then compared to the known output feature of the data entry to see whether or not the prediction provided by the trained classifier is correct.

By way of example, the classifier algorithms used include the logistic regression (LR) model 35, the deep learning (DL) model 36, the decision trees (DT) model 37, the random forest (RF) model 38 and the gradient boosted tree (GBT) model 39. The models may be provided by open source platforms. In particular, the DL model 36 may be based on a multi-layer feedforward artificial neural network that is trained with stochastic gradient descent using backpropagation. The GBT model 39 may be a forward learning ensemble method, in which regression trees on all the features of the dataset are built sequentially in a fully distributed way.

The performances of the five models with respect to Class 1 classification are shown in FIG. 8. This means that the output variables (Y) in this instance include the Class 1 labels of the data samples only. The performance indicators include accuracy 41, precision 42 and recall 43. The accuracy 41 represents the fraction of correct predictions provided by a classifier model. The precision 42 represents the fraction of correct positive predictions provided by a classifier model. The recall 43 represents the fraction of correct predictions of actual positives. These indicators are commonly used to assess the performance of a classifier.

As shown in FIG. 8, the GBT model provides the best performance among all of the models used. In particular, the GBT model achieves a great accuracy value of 94.6%, a precision value of 95.4% and a recall value of 95.6%.

An assessment of the top 20 strongest input variables and their corresponding weights with respect to Class 1 classification are listed in Table 1 below.

TABLE 1

Input variables and weights with respect to Class 1 classification

| | Input variables | Weight |
|---|---|---|
| 1 | w30_genhurst | 1.000 |
| 2 | w10_genhurst | 0.947 |
| 3 | w5_genhurst | 0.886 |
| 4 | w1_genhurst | 0.877 |
| 5 | w15s_genhurst | 0.877 |
| 6 | w30s_genhurst | 0.877 |
| 7 | w2_genhurst | 0.868 |
| 8 | w10_w4_mean | 0.768 |
| 9 | w10_noise_brown | 0.678 |
| 10 | w10_skewness | 0.637 |
| 11 | w30_skewness | 0.615 |
| 12 | w1_w4_mean | 0.601 |
| 13 | w15s_w4_mean | 0.601 |
| 14 | w30s_w4_mean | 0.601 |
| 15 | w5_skewness | 0.580 |
| 16 | w10_noise_white | 0.565 |
| 17 | w5_noise_pink | 0.533 |
| 18 | w5_noise_white | 0.530 |
| 19 | w2_w1_max | 0.525 |
| 20 | w2_noise_pink | 0.523 |

With reference to Table 1, Variables 1 to 7 refer to the generalised Hurst exponents extracted from data segments which have temporal lengths of 30 minutes, 10 minutes, 5 minutes, 1 minute, 15 seconds, 30 seconds, 2 minutes, respectively. As described above, the temporal lengths of data segments are determined by the window sizes of window functions applied to the raw data. Variable 8 ("w10_w4_mean") refers to the mean value of the coefficients extracted at level-4 of a wavelet decomposition (e.g., an 8-level wavelet decomposition) performed on a data segment which is of a temporal length of 10 minutes.

Variable 9 ("w10_noise_brown") refers to the power of the brown noise contained within a data segment which is of a temporal length of 10 minutes. Variables 10 ("w10_skewness"), 11 ("w30_skewness") and 15 ("w5_skewness") refer to the skewnesses of data segments which have temporal lengths of 10 minutes, 30 minutes and 5 minutes, respectively. Variables 12 to 14, i.e., "w1_w4_mean", "w15s_w4_mean", "w30s_w4_mean", refer to the mean values of the coefficients extracted at level-4 of wavelet decompositions (e.g., 8-level wavelet decompositions) performed on data segments which are of temporal lengths of 1 minute, 15 seconds and 30 seconds, respectively. Variables 16 ("w10_noise_white") and 18 ("w5_noise_white") refer to the power levels of the white noise contained within data segments which are of temporal lengths of 10 minutes and 5 minutes, respectively. Variables 17 ("w5_noise_pink") and 20 ("w2_noise_pink") refer to the power levels of the pink noise contained within data segments which are of temporal lengths of 5 minutes and 2 minutes, respectively. Variable 19 ("w2_w1_max") refers to the max value of the coefficients extracted at level-1 of a wavelet decomposition (e.g., an 8-level wavelet decomposition) performed on a data segment which is of a temporal length of 2 minutes.

The above results indicate that the generalised Hurst exponents extracted from the data segments, regardless of the temporal lengths of the data segments, are strong input variables and play an important role in determining the lighting conditions (e.g., "day" or "night") of plants. The above results further demonstrate that the lighting conditions of plants can be accurately predicted (or assessed) by a classifier solely based upon the electrical signals obtained from the plants.

Further, from Table 1, it appears that the power levels of noise contained within data segments, the skewness of data segments, as well as statistical features (e.g., max, mean) of the coefficients obtained by wavelet decomposition (in particular, the level-1 and level-4 coefficients of the wavelet decomposition) also play an important role in determining the lighting conditions of plants.

The performances of the five classifier models with respect to Class 2 classification are shown in FIG. 9. This means that the output variables (Y) in this instance include the Class 2 labels (e.g., "normal" or "water stressed") of the data samples only. The performance indicators include accuracy 41, precision 42 and recall 43. As shown in FIG. 9, the GBT model again provides the best performance among all of the models used. In particular, the GBT model achieves a great accuracy value of 98.5%, a precision value of 99.3% and a recall value of 98.5%.

TABLE 2

Input variables and weights with respect to Class 2 classification

| | Input variables | Weight |
|---|---|---|
| 1 | w5_genhurst | 1.000 |
| 2 | w30_genhurst | 0.999 |
| 3 | w10_genhurst | 0.999 |
| 4 | w2_genhurst | 0.949 |
| 5 | w15s_genhurst | 0.859 |
| 6 | w30s_genhurst | 0.859 |
| 7 | w1_genhurst | 0.859 |
| 8 | w15s_w1_max | 0.774 |
| 9 | w30s_w1_max | 0.774 |
| 10 | w1_w1_max | 0.774 |
| 11 | w15s_w1_min | 0.759 |
| 12 | w30s_w1_min | 0.759 |
| 13 | w1_w1_min | 0.759 |
| 14 | w5_w1_min | 0.726 |
| 15 | w2_w1_min | 0.725 |
| 16 | w10_w1_min | 0.706 |
| 17 | w15s_interquartile | 0.691 |
| 18 | w30s_interquartile | 0.691 |
| 19 | w1_interquartile | 0.691 |
| 20 | w2_w1_max | 0.667 |

An assessment of the top 20 strongest input variables and their corresponding weights with respect to Class 2 classification are listed in Table 2 above.

With reference to Table 2, Variables 1 to 7 refer to the generalised Hurst exponents extracted from data segments which have temporal lengths of 5 minutes, 30 minutes, 10 minutes, 2 minutes, 15 seconds, 30 seconds, 1 minute, respectively. Variables 8 to 10, i.e., "w15s_w1_max", "w30s_w1_max", "w1_w1_max", refer to the max values of the coefficients extracted at level-1 of wavelet decompositions (e.g., 8-level wavelet decompositions) performed on data segments which are of temporal lengths of 15 seconds, 30 seconds, and 1 minute, respectively. Variables 11 to 16 refer to the min values of the coefficients extracted at level-1 of wavelet decompositions (e.g., 8-level wavelet decompositions) performed on data segments which are of temporal lengths of 15 seconds, 30 seconds, 1 minute, 5 minutes, 2 minutes and 10 minutes, respectively. Variables 17 to 19, i.e., "w15s_interquartile", "w30s_interquartile" and "w1_interquartile" refer to the interquartile ranges of data segments which are of temporal lengths of 15 seconds, 30 seconds, and 1 minute, respectively. Variable 20 ("w2_w1_max") refers to the max value of the coefficients extracted atlevel-1 of a wavelet decomposition (e.g., an 8-level wavelet decomposition) performed on a data segment which is of a temporal length of 2 minutes.

Among the above listed input variables, the generalised Hurst exponents extracted from the data segments, regardless of the temporal lengths of the data segments, are strong input variables and play an important role in determining the water stress statuses (e.g., "normal" or "water stressed") of plants. The above results further demonstrate that the water stress statuses of plants can be predicted or assessed, with a high-degree of confidence, by a classifier solely based upon the electrical signals obtained from the plants.

Further, from Table 2, it appears that the statistical features (e.g., max, min) of the coefficients extracted at level-1 of wavelet decompositions performed on data segments (in particular those having a temporal length of not greater than 10 minutes) as well as the interquartile ranges of data segments (in particular those having a temporal length of not greater than 1 minute) also play an important role in determining the water stress statuses of plants.

It will be appreciated that the results shown in Table 1 and Table 2 are based upon the particular dataset gathered and the particular classifier being used, and that a different dataset (e.g., which is obtained from different plants and/or for predicting a different plant status) or a different machine learning model may result in different dominating input variables and different weightings.

The results shown in FIGS. 8 and 9 as well as Tables 1 and 2 prove that machine-learning algorithms provide good classification performance and also confirm that the electrical signals obtained from plants contain useful patterns for identifying potential plant stress conditions.

Further, while the examples provided above are for binary classification (in which the plant status is classified into one of two classes, such as, "normal" or "water stressed"), it will be appreciated that supervised machine learning algorithms can be used to perform multinomial classification (in which the plant status is classified into one of three or more classes) or even regression (in which the plant status is predicted within a continuous output). This depends upon the particular training dataset and the particular machine learning model being used for performing the prediction. For example, each data entry in a training dataset may be labelled with a corresponding value (e.g., any value within 0% to 100%) indicating a percentage of the actual irrigation received as compared to the full amount of irrigation. This particular training dataset may be used to train a regression model which predicts the percentage of irrigation received by a plant. In another example, each data entry in the training dataset may be labelled with a lighting condition selected from the group of "no lighting", "strong lighting" and "weak lighting". This particular training dataset may be used to train a multinomial classifier. Using the trained multinomial classifier, the lighting condition of a plant may be classified into one of three classes (i.e., "no lighting", "strong lighting" and "weak lighting").

It will further be appreciated that supervised machine learning algorithms can be used to predict (or assess) many types of plant statuses which are in no way limited to the lighting condition or the water stress status of a plant. In general, it is expected that a characteristic of a plant can be predicted with a reasonable-degree of confidence by a machine learning model solely based upon the electrical signal obtained from the plant.

Figure 10:
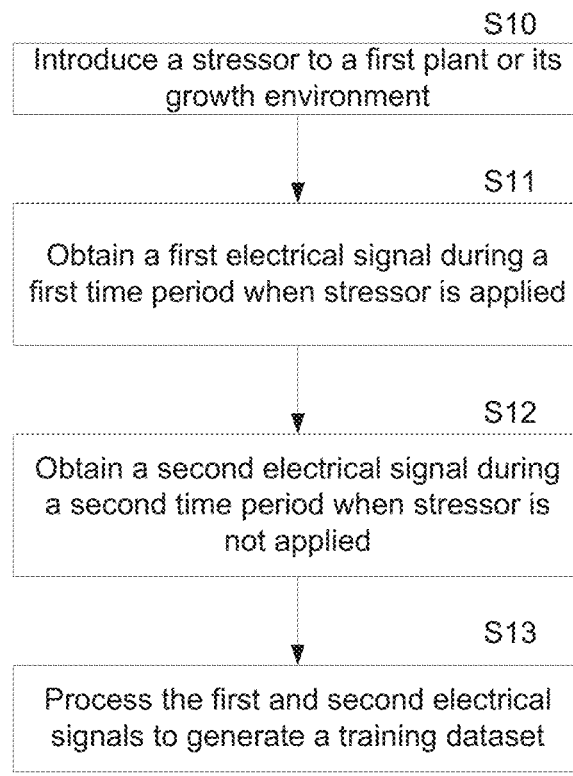
FIG. 10 is a flowchart showing processing steps carried out to generate a training dataset for use to train a machine learning model.

FIG. 10 illustrates a flowchart showing processing steps carried out to generate a training dataset for use to train a machine learning model.

At step S10, a stressor is introduced to a first plant or a growth environment (e.g., the environment 50) of the first plant. The variety of the first plant and the type of the stressor may be suitably chosen depending upon the needs of a plant grower. In general, the growth environment of the first plant may be growing chambers, greenhouses or fields, and the first plant may be cultivated under controlled conditions to simulate normal growing environments. The stressor is introduced purposely to simulate natural occurrences.

The stressor may be any factor which causes a change to the growth environment or the physiology of the first plant. Typical examples of a change to the growth environment include a change to the lighting condition of the first plant, a change to the irrigation of the first plant (which, for example, may be caused by switching on/off an irrigation pump), a change to the application of nutrients to the first plant (which, for example, may be caused by switching on/off a nutrigation pump), a change to the ambient temperature of the first plant, a change to the ambient humidity of the first plant, a change to the ambient $CO_2$ level of the first plant, a change to the ambient pollutant (e.g., hydrogen sulphide or dust) level of the first plant, or a change to the chemical composition (e.g., the salt level) of the growth medium. Typical examples of a change to the physiology of the first plant include an introduction of a substance (e.g., an insect or other pest, a chemical substance, or a pathogen which may be a virus, fungus or bacteria, etc.) which pose a threat to the first plant, and a change to prematurely cause or delay growth, flowering, or fruit maturing of the first plant, etc. The substance may be directly applied to a part (e.g., leaf, stem or root) of the first plant.

The first plant may be one or more plants. Preferably, the first plant may include a plurality of plants which tend to provide better statistical results than a single plant.

At step S11, a first electrical signal is obtained from the first plant during a first time period when the stressor is applied to the growth environment of the first plant.

At step S12, a second electrical signal is obtained from the first plant during a second time period when the stressor is not being applied to the growth environment of the first plant.

Steps S10 to S12 may take any suitable temporal order which is not limited to the sequence shown in FIG. 10. For example, the obtaining of the second electrical signal at step 12 may be performed first, followed by an introduction of the stressor at step S10 and the obtaining of the first electrical signal at step S11.

The first and second electrical signals may be raw data obtained by the leads 6, 8 of the plant health monitoring device 1 described above. In particular, the device 1 may operate outside of a Faraday cage. The first time period and the second time period collectively form the monitoring time of the first plant. Alternatively, the first and second electrical signals may be digitised signals output by the ADC 14 of the device 1 and may be in the time domain.

At step S13, the first electrical signal and the second electrical signal are processed to generate a training dataset. Step S13 may be carried out by the device 1 and/or an external computer/server which is connected to the device 1 via the network interface 12f of the device 1. Alternatively, step S13 may be carried out by any suitable device(s) to which the first electrical signal and the second electrical signal are provided.

The data pre-processing steps shown in FIG. 7 may be used to process the first and second electrical signals at step S13. In particular, the first and second electrical signals are processed by steps S1 to S5 sequentially. After step S5, a training dataset is generated as described above.

Step S4 requires that each data sample is labelled with a corresponding characteristic of the first plant. The labels of the data samples may be obtained by monitoring a physiological marker of the first plant and/or an environmental condition of the first plant during the first and second time periods. The physiological marker may include, for example, the leaf turgor pressure, the stage of development of the plant, the stem diameter, the leaf fluorescence, the leaf temperature, and/or the leaf colour, etc. The environmental condition includes, for example, the ambient lighting condition, the ambient $CO_2$ level, the air temperature, and/or the soil water content, etc. The monitoring may be implemented by any suitable sensor available in the market. The particular physiological marker and/or environmental condition being monitored depend upon the nature of the stressor introduced at step S10. For example, if the stressor causes a change to the irrigation of the first plant, a leaf turgor sensor may be employed to monitor the leaf turgor pressure (i.e., a physiological marker) of the first plant, or a soil water sensor may be used to monitor the soil water content of the first plant. The obtained leaf turgor pressure or the obtained soil water content may be used as labels to label the data samples at step S4. In addition, depending upon the particular type of the stressor introduced, the ambient lighting condition, the ambient humidity level, the ambient pollutant level, the ambient $CO_2$ level, the chemical composition of the growth medium, the presence of pests, and/or the air temperature of the first plant may be monitored using, for example, a light sensor, a humidity sensor, a pollution sensor, a $CO_2$ sensor, a chemical sensor, a pest detection sensor, and/or a temperature sensor, respectively, to generate the labels used at step S4.

In the event that more than one stressor has been introduced to the growth environment of the first plant, it will be appreciated that each data sample may have more than one label which indicates more than one characteristic of the first plant. In that case, all of the labels of each data sample collectively form the output features of the generated training dataset.

Alternatively, the labels of the data samples may be obtained solely based upon the presence and the absence of the stressor. This is because the stressor typically causes the first plant to have a corresponding characteristic (e.g., light deficit/excess, water deficit/excess, nutrition deficit/excess, slow/fast metabolism, temperature deficit/excess, CO2 deficit/excess, salt deficit/excess, insect infestation or pathogen presence where a pathogen may be a virus, fungus or bacteria, etc.) associated with the nature of the stressor. Therefore, it is possible to derive a status of the first plant based upon the presence/absence of the stressor without requiring further sensors (such as those sensing the physiological marker and/or the environmental condition of the first plant). The derived statuses of the first plant may be used to label the data samples at step S4. For example, it may be assumed that the first plant has a "water deficit" status during the first time period when a stressor of switching off irrigation pump is applied, and has a "normal" status during the second time period when the same stressor is not applied. However, it will be understood that a training dataset obtained by labelling the data samples using the derived "binary" statuses may not be ideal for training all kinds of supervised machine learning algorithms (such as, multinomial classification or regression algorithms).

The data pre-processing steps shown in FIG. 7 include a normalisation step at step S5. When the first and second electrical signals are obtained from multiple plants (which collectively form the "first plant"), step S5 may be useful to normalise the extracted characterising features of the data samples obtained across different plants, because the electrical signals obtained from different plants may have different amplitudes. When the first and second electrical signals are obtained from a single plant (which forms the "first plant") at multiple different times, at multiple different parts of the plant, and/or when the plant is at multiple different locations, step S5 may be useful to eliminate any variations in the amplitude of the electrical signals obtained at different times/parts/locations but under the same stressor condition. It will, however, be appreciated that step S5 is optional for the generation of a training dataset.

Further, the data pre-processing steps shown in FIG. 7 include a signal conditioning step at step S1. It will be appreciated that depending upon the quality of the first and second electrical signals, step S1 may be omitted. For example, if the first and second electrical signals are those output by the data acquisition module 10 of the device 1 which already performs amplification, digitisation, analog/digital filtering and decimation to the raw signal, then step S1 may be dispensed with.

In an example, the training dataset may also comprise environmental data characterising the growth environment of the first plant during the first and the second time periods. In such an embodiment, the flowchart of FIG. 10 may further include additional processing steps such as, for example: a step of obtaining the environmental data characterising the growth environment of the first plant during the first time period when the stressor is applied to the growth environment of the first plant, and a step of obtaining the environmental data characterising the growth environment of the first plant during the second time period when the stressor is not being applied to the growth environment of the first plant. The environmental data may, for example, comprise one or more of: data indicative of a light intensity in the growth environment, data indicative of soil water content of the growth environment, data indicative of a temperature (e.g., an air temperature) of the growth environment, data indicative of a humidity level of the growth environment, etc. The environment data may be directly output by available sensors located in the growth environment, or may be processed sensor data.

The environmental data may be processed together with the first and second electrical signals at step S13 to generate the training dataset. The data pre-processing steps shown in FIG. 7 may be used to process the environmental data and the first and second electrical signals at step S13. In particular, the environmental data may be labelled with a corresponding characteristic of the first plant in the same way as the labelling of the data samples as described above. The environmental data may further be normalised at step S5 to remove undesired variations.

Figure 11:
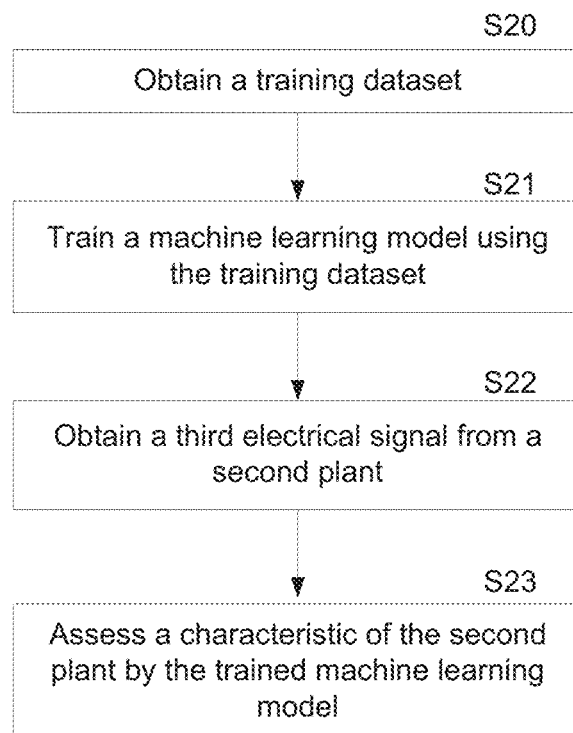
FIG. 11 is a flowchart showing processing steps carried out to assess a characteristic of a plant using a training dataset and a machine learning model.

FIG. 11 illustrates a flowchart showing processing steps carried out to assess a characteristic of a plant using a training dataset and a machine learning model.

At step S20, a training dataset is obtained. The training dataset may be generated by the processing steps as shown in FIG. 10, or may be generated in other suitable ways. For example, during long-term monitoring of plants, a plant grower may have accumulated data comprising electrical signals obtained from plants and corresponding physiological markers and/or environmental condition data of the plants. While the plant grower did not intentionally introduce any stressor to the plants or the growth environment of the plants, stressors naturally occur during a part of the monitoring period. Thus, the data accumulated by the plant grower may be processed according to step S13 of FIG. 10 to generate a training dataset. Step S20 may be performed by any suitable computer/server.

In general, each data entry within the training dataset includes input features which characterise or are derived from the electrical signals obtained from a plant, and at least one output feature indicative of a known characteristic of the plant. It will be appreciated that the input features are obtained by processing the plant's electrical signals. In this way, a machine learning model trained by the training dataset can be used to predict an unknown characteristic of a particular plant based upon electrical signals obtained from that plant.

Each data entry may have multiple output features indicative of multiple types of characteristics of the plant. The multiple types of characteristics may be associated with the presence/absence of multiple stressors within the plant or the growth environment of the plant. A training dataset having such data entries can be used for training a machine learning model having multiple output variables. The trained model may be useful to predict multiple types of unknown characteristics of a particular plant based upon the electrical signals obtained from that plant.

Further, the training dataset includes at least one data entry when a stressor is present within a plant or its growth environment, and at least one data entry when the same stressor is not present within the plant or its growth environment. Accordingly, the electrical signals of the plant can be distinguished with respect to the presence/absence of the stressor.

The training dataset may include first data characterising a first electrical signal obtained from a first plant during a first time period when a stressor is present in the first plant or a growth environment of the first plant, second data characterising a second electrical signal obtained from the first plant during a second time period when a stressor is not present in the first plant or the growth environment of the first plant, and third data indicative of a characteristic of the first plant during the first time period and a characteristic of the first plant during the second time period.

The first data may be extracted characterising features of data sample obtained from the first electrical signal at step S3 of FIG. 7 or the normalised version of the extracted characterising features if step S5 of FIG. 7 takes place. The second data may be extracted characterising features of data sample obtained from the second electrical signal at step S3 of FIG. 7 or the normalised version of the extracted characterising features if step S5 of FIG. 7 takes place. The third data may comprise labels of the data samples used at step S4 of FIG. 7 and described above.

At step S21, the training dataset obtained at step S20 is used to train a machine learning model. The machine learning model may be a regression model or a classification model (i.e., a classifier). The classifier may be a binary classifier or a multinomial classifier. Further, the classifier may be a linear classifier. For example, the linear classifier may be Support Vector Machine (SVM) with a linear kernel or may be logistic regression based. Alternatively, the classifier may be a non-linear classifier such as a neural network. In a particular example, the machine learning model may be a gradient boosted tree (GBT) model as described above. Step S21 may be performed by any suitable computer/server.

The input variables (X) of the machine learning model may correspond to the types of the first/second data characterising the first/second electrical signal. The output variables (Y) of the machine learning model may correspond to the type(s) of the third data indicating characteristics of plants. Each of the input variables has a corresponding weight, which indicates the strength of the respective input variable in determining the output variables. Training a machine learning model basically means calibrating all of the weights.

After the machine learning model is trained, the model or a part of the model may be uploaded to the device 1 or an external computer/server which is connected to the device 1 via the network interface 12f of the device 1.

At step S22, a third electrical signal is obtained from a second plant. The third electrical signal may be obtained by the plant health monitoring device 1. In particular, the third electrical signal may be digitised signals output by the ADC 14 of the device 1 and may be in the time domain. The second plant is preferably, but not necessarily, of the same plant variety as the first plant from which the training dataset is derived. It has been found that a training dataset obtained from plant(s) of a particular plant variety can be used to train a machine learning model for assessing a characteristic of plant(s) of a different plant variety.

At step S23, the trained machining learning model is used to assess a characteristic of the second plant based upon the third electrical signal. This may require processing the third electrical signal to generate input data corresponding to the input variables of the model. The input data may be data characterising the third electrical signal. In an example, the third electrical signal may be processed according to steps S1 to S3 of FIG. 7 to extract features characterising the third electrical signal and the extracted features are the input data. The input data is then fed into the trained model, and the output data of the model indicates the predicted characteristic of the second plant. The characteristic of the second plant may be assessed in near real-time if the trained model is loaded to the device 1 or an external computer/server which is connected to the device 1.

In the event that the training dataset obtained at step S20 includes environmental data characterising the growth environment of the first plant during the first and the second time periods, it will be appreciated that an additional step of obtaining environmental data characterising a growth environment of the second plant may be included before step S23 takes place. The obtained environmental data is preferably of the same type as the environment data included in the training dataset. Subsequently, the trained machine learning model is used to assess the characteristic of the second plant based upon the third electrical signal and the obtained environmental data characterising the growth environment of the second plant. That is, the environmental data characterising the growth environment of the second plant may also be provided as input data to the trained machine learning model.

Figure 12:
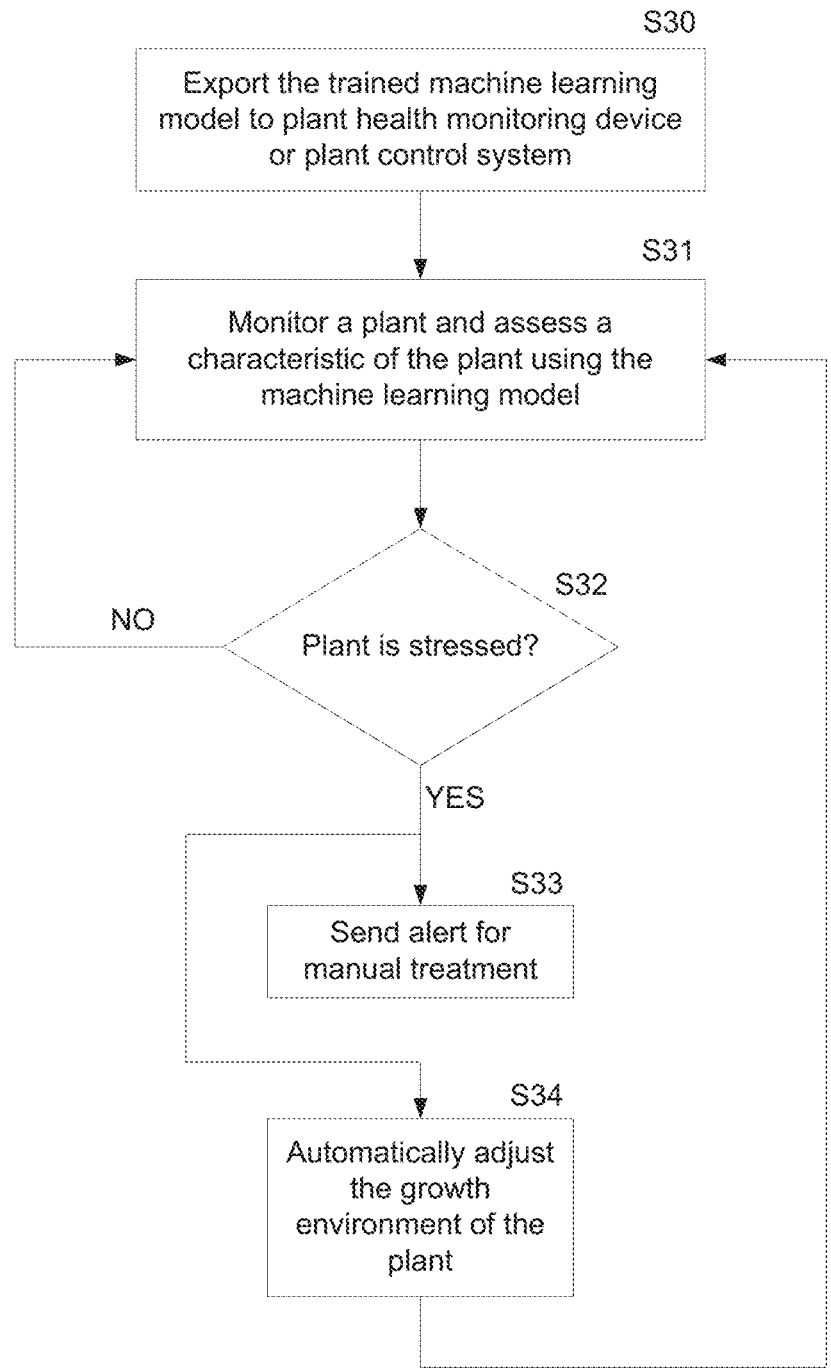
FIG. 12 is a flowchart showing processing steps carried out to monitor a characteristic of a plant and to automatically adjust a growth environment of the plant.

FIG. 12 illustrates a flowchart showing processing steps carried out to monitor a characteristic of a plant and to adjust a growth environment of the plant.

At step S30, at least a part of the machine learning model trained at step S21 of FIG. 11 is exported to a plant health monitoring device 1 or a plant control system (for example, the plant control device 100) as shown in FIG. 1.

At step S31, the plant health monitoring device 1 obtains an electrical signal from a plant. The device to which the trained model is exported (e.g., the plant health monitoring device 1 and/or the plant control device 100) assesses a characteristic of the plant using the trained machine learning model and the obtained electrical signal, and may generate plant data indicative of an assessment result of the characteristic of the plant. The plant data may be an output of the trained machine learning model, or may be generated based upon the output of the trained machine learning model.

At step S32, the plant data is analysed to determine whether the plant is stressed (i.e., whether a stressor is present within the plant or the growth environment of the plant). This step may be performed by the device to which the trained model is exported (e.g., the plant health monitoring device 1 and/or the plant control device 100) or by another device connected thereto.

When it is determined at step S32 that the plant is not stressed, then the processing proceeds back to step S31 in which the plant health monitoring device 1 and the plant control system continue to monitor the plant and to assess the characteristic of the plant.

When it is determined at step S32 that the plant is stressed, the processing proceeds to perform one or both of steps S33 and S34.

At step S33, the plant control device 100 sends an alert to the plant grower by, for example, sending a message to the mobile phone of the grower. The alert allows the plant grower to make an informed decision and prompts the grower to perform manual treatment to the plant if it is deemed necessary. The alert may include information indicative of the plant data.

At step S34, the plant control device 100 may cooperate with other devices of the plant control system (e.g., the light source 51, the irrigation system 52, a nutrigation pump, a heating source, a fan, a vent, and a pesticide pump, etc.) to automatically change the growth environment of the plant based upon the plant data. In particular, the plant control device 100 may generate a plant control signal which triggers events, such as, adjusting the operation of an irrigation/nutrigation pumps, heaters, fans or lightings, altering vent positions, adjusting the operation of pumps which deliver chemical substances to the growth medium and/or a pesticide pump, so as to automatically adjust the growth environment of the plant. Following step S34, the processing proceeds to step S31 where the plant health monitoring device 1 and the plant control system continue to monitor the plant and to assess the characteristic of the plant.

The method and system described above provides an efficient agronomic tool which allows the plant growers to accurately monitor the health/vitality of plants and to take preventive measures before initial symptoms appear on the plants.

The machine learning model trained at step S21 of FIG. 11 may also be exported to a diagnostic device. The diagnostic device may have the functionality of the plant health monitoring device 1, thus being able to obtain electrical signals from plants using electrodes and leads. The diagnostic device may further be able to perform step S23 of FIG. 11 so as to identify the presence/absence of stressor(s) within a plant or its growth environment. The diagnostic device may have a display configured to show plant data indicative of an assessment result of the plant. The plant data may be used by the plant grower to identify stressed plants. The diagnostic device may preferably be portable. It will be appreciated that subject to the limited computational power of a portable device, the diagnostic device may be limited to identify the presence of a specific stressor, or limited set of stressors, only.

Optionally, more than one machine learning model trained at step S21 may be exported to the diagnostic device. The multiple machine learning models stored in the diagnostic device may be trained using different training datasets.

In an example, the plurality of machine learning models stored in the diagnostic device may each be for assessing different characteristics of a plant. For instance, the diagnostic device may store a first machine learning model for assessing a nutrient insufficiency or a growth condition of a plant. The first machine learning model may be trained using a training dataset comprising environmental data, such as, data indicative of a light intensity in the growth environment and data indicative of soil water content of the growth environment. These particular environmental factors are known to be correlated with the growth of a plant. The diagnostic device may further store a second machine learning model for assessing whether a plant is infested by insects. The second machine learning model may be trained using a training dataset comprising environmental data, such as, data indicative of a temperature (e.g., an air temperature) of the growth environment. The diagnostic device may further store a third machine learning model for assessing whether a plant is infected with a pathogen (e.g., fungus). The third machine learning model may be trained using a training dataset comprising environmental data, such as, data indicative of a humidity level of the growth environment. In order to use a particular one of the stored machine learning models to assess a corresponding characteristic of a plant, environmental data which characterises a condition of a growth environment of the plant and which is also of the same type as that used to train the model may be provided. Accordingly, the received environmental data and the electrical signals obtained from the plant to be assessed are fed to the input layer of the trained model to assess the characteristic of the plant.

In an alternative example, the multiple machine learning models stored in the diagnostic device may be for assessing the same characteristic of a plant. For instance, the plurality of machine learning models may include a first model which has been trained with a first training dataset, and a second model which has been trained with a second training dataset. The first training dataset may include first environmental data characterising a first condition of the growth environment. The second training dataset may include second environmental data characterising a second different condition of the growth environment. In each model, the environmental data is fed into the input layer of the model to train the model. As such, when the diagnostic device receives particular environment data of a plant to be assessed and electrical signals obtained from the plant, the diagnostic device determines the type of the received environment data, and selects one of the stored models based upon the received environment data. In this way, the diagnostic device can select a suitable machine learning model for assessing the characteristic of the plant based upon the available environmental data.

It will of course be understood that the number of machine learning models and/or categories of environmental data used may be varied. Moreover, various (and possibly overlapping) combinations of environmental data may be used with different machine learning models. For example, temperature and humidity data may be used to train a first machine learning model for assessing a first characteristic of a plant, while temperature and light intensity data may be used to train a second machine learning model for assessing a second characteristic of a plant.

In general terms, it will be understood that where it is described herein that a characteristic of a plant is assessed, or the presence/absence of a stressor within a plant or its growth environment is identified, such an assessment or identification may also be referred to as a diagnosis (e.g. a diagnosis of a particular health condition of a plant being present). Similarly, an assessment or identification may be referred to as a prediction (e.g. a prediction of a particular condition or status of a plant being present).

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

The invention claimed is:

1. A method of assessing a characteristic of a plant, comprising:
obtaining a training dataset, wherein the training dataset comprises first data characterising a first electrical signal obtained from a first plant during a first time period when a stressor is present in the first plant or in a growth environment of the first plant, the first electrical signal indicative of bioelectrical activity within the first plant, second data characterising a second electrical signal obtained from the first plant during a second time period when a stressor is not present in the first plant or in the growth environment of the first plant, the second electrical signal indicative of bioelectrical activity within the first plant, and third data indicative of a characteristic of the first plant during the first time period and a characteristic of the first plant during the second time period, wherein obtaining the training dataset further comprises:
obtaining data samples from the first electrical signal at a predetermined sampling frequency, wherein at least one of the data samples comprises a data segment obtained by applying a window function to the first electrical signal; and
extracting at least one characterising feature from each data segment, and wherein the first data comprises the at least one characterising feature, wherein the at least one characterising feature comprises a generalized Hurst exponent;
training a machine learning model based upon the training dataset;
obtaining a third electrical signal from a second plant, the third electrical signal indicative of bioelectrical activity within the second plant; and
assessing, using the trained machine learning model, a characteristic of the second plant based upon the third electrical signal;
wherein the first, second, and third electrical signals are obtained by one or more capture devices, the one or more capture devices comprising first and second electrodes.

2. The method of claim 1, wherein obtaining the training dataset comprises:
introducing the stressor to the first plant or the growth environment of the first plant;
obtaining the first electrical signal from the first plant during the first time period when the stressor is being applied to the first plant or the growth environment of the first plant; and
obtaining the second electrical signal from the first plant during the second time period when the stressor is not applied to the first plant or the growth environment of the first plant.

3. The method of claim 1, wherein obtaining the training dataset further comprises:
processing the first electrical signal to generate the first data, and
processing the second electrical signal to generate the second data.

4. The method of claim 3, wherein processing the first electrical signal to generate the first data comprises:
performing signal conditioning on the first electrical signal.

5. The method of claim 1, wherein obtaining the training dataset further comprises:
labelling the data samples using the third data.

6. The method of claim 1, wherein:
obtaining the training dataset further comprises labelling the data samples using the third data; and
the training dataset comprises a plurality of data entries, at least one of which comprising the at least one characterizing feature extracted from a respective data sample and a label of the same data sample.

7. The method of claim 1, wherein the stressor is configured to at least one of:
affect a lighting condition of the first plant;
cause the first plant to have water stress,
cause the first plant to be infested by insects;
cause the first plant to be infected with a pathogen;
cause the first plant to have $CO_2$ deficit;
cause the first plant to have excess or insufficient nutrients;
cause the first plant to have temperature stress;
cause the first plant to have salt stress; and
prematurely cause or delay growth, flowering, or fruit maturing of the first plant.

8. The method of claim 1, wherein assessing a characteristic of the second plant based upon the third electrical signal comprises:
processing the third electrical signal to generate data characterising the third electrical signal; and
providing the generated data as input data to the trained machine learning model.

9. The method of claim 1, wherein the training dataset further comprises environmental data characterising the growth environment of the first plant during the first and the second time periods.

10. The method of claim 9, further comprising:
obtaining environmental data characterising a growth environment of the second plant;
assessing, using the trained machine learning model, the characteristic of the second plant based upon the third electrical signal and the environmental data characterising the growth environment of the second plant.

11. The method of claim 1, further comprising:
generating plant data indicative of an assessment result of the characteristic of the second plant.

12. The method of claim 11, further comprising:
generating a plant control signal based upon the plant data, wherein the plant control signal is configured to change a growth environment of the second plant.

13. An apparatus for assessing a characteristic of a plant comprising:
a non-transitory computer readable storage medium storing a machine learning model, wherein the machine learning model has been trained using a training dataset, wherein the training dataset comprises first data characterising a first electrical signal obtained from a first plant during a first time period when a stressor is present in the first plant or in a growth environment of the first plant, the first electrical signal indicative of bioelectrical activity within the first plant, second data characterising a second electrical signal obtained from the first plant during a second time period when a stressor is not present in the first plant or in the growth environment of the first plant, the second electrical signal indicative of bioelectrical activity within the first plant, and third data indicative of a characteristic of the first plant during the first time period and a characteristic of the first plant during the second time period, wherein obtaining the training dataset comprises:
obtaining data samples from the first electrical signal at a predetermined sampling frequency, wherein at least one of the data samples comprises a data segment obtained bv applying a window function to the first electrical signal; and
extracting at least one characterising feature from each data segment and wherein the first data comprises the at least one characterising feature, wherein the at least one characterising feature comprises a generalized Hurst exponent:
a capture device comprising first and second electrodes configured to sense a third electrical signal from a second plant, the third electrical signal indicative of bioelectrical activity within the second plant; and
a processor configured to assess a characteristic of the second plant based upon the machine learning model and the third electrical signal.

14. The apparatus of claim 13,
wherein the non-transitory computer readable storage medium is configured to store a first machine learning model which has been trained by a first training dataset for assessing a first characteristic of a plant, and a second machine learning model which has been trained by a second training dataset for assessing a second different characteristic of a plant, and wherein the first training dataset further comprises first environmental data characterising a first condition of the growth environment, and the second training dataset further comprises second environmental data characterising a second different condition of the growth environment.

15. The apparatus of claim 13,
wherein the non-transitory computer readable storage medium is configured to store a first machine learning model which has been trained by a first training dataset for assessing a first characteristic of a plant, and a second machine learning model which has been trained by a second training dataset for assessing the first characteristic of a plant, and wherein the first training dataset further comprises first environmental data characterising a first condition of the growth environment, and the second training dataset further comprises second environmental data characterising a second different condition of the growth environment.

16. A system comprising:
an apparatus according to claim 13, and
a plant control system configured to automatically change a growth environment of the second plant based upon the assessed characteristic of the second plant.

17. A method of training a machine learning model for assessing a characteristic of a plant, the method comprising:
obtaining a training dataset, wherein the training dataset comprises first data characterising a first electrical signal obtained from a first plant during a first time period when a stressor is present in the first plant or in a growth environment of the first plant, the first electrical signal indicative of bioelectrical activity within the first plant, second data characterising a second electrical signal obtained from the first plant during a second time period when a stressor is not present in the first plant or in the growth environment of the first plant, the second electrical signal indicative of bioelectrical activity within the first plant, and third data indicative of a characteristic of the first plant during the first time period and a characteristic of the first plant during the second time period, wherein obtaining the training dataset further comprises:
obtaining data samples from the first electrical signal at a predetermined sampling frequency, wherein at least one of the data samples comprises a data segment obtained by applying a window function to the first electrical signal; and
extracting at least one characterising feature from each data segment, and wherein the first data comprises the at least one characterising feature, wherein the at least one characterising feature comprises a generalized Hurst exponent; and
training the machine learning model, using the training dataset, to assess a characteristic of a second plant based upon a third electrical signal obtained from the second plant, the third electrical signal indicative of bioelectrical activity within the second plant;
wherein the first, second, and third electrical signals are obtained by one or more capture devices, the one or more capture devices comprising first and second electrodes.

* * * * *